(12) United States Patent
Nebolsin et al.

(10) Patent No.: US 8,906,897 B2
(45) Date of Patent: Dec. 9, 2014

(54) ANTIMICROBIAL AGENTS BASED ON HEMIN DERIVATIVES

(75) Inventors: Vladimir Evgenievich Nebolsin, Moscow (RU); Galina Alexandrovna Zheltukhina, Moscow (RU)

(73) Assignee: Obschestvo S Ogranichennoi Otvetstvennostiyu "Pharmenterprises", Moscow (RU)

(*) Notice: Subject to any disclaimer, the term of this patent is extended or adjusted under 35 U.S.C. 154(b) by 8 days.

(21) Appl. No.: 13/395,149

(22) PCT Filed: Sep. 8, 2010

(86) PCT No.: PCT/RU2010/000488
§ 371 (c)(1),
(2), (4) Date: Jul. 2, 2012

(87) PCT Pub. No.: WO2011/031187
PCT Pub. Date: Mar. 17, 2011

(65) Prior Publication Data
US 2012/0264724 A1    Oct. 18, 2012

(30) Foreign Application Priority Data
Sep. 10, 2009    (RU) .............................. 2009133914

(51) Int. Cl.
| A61K 31/555 | (2006.01) |
| A61K 38/00 | (2006.01) |
| C07D 487/22 | (2006.01) |
| C07F 15/02 | (2006.01) |
| C07K 14/795 | (2006.01) |
| C07K 14/805 | (2006.01) |

(52) U.S. Cl.
CPC ............ *C07D 487/22* (2013.01); *A61K 31/555* (2013.01); *C07F 15/025* (2013.01); *C07K 14/795* (2013.01); *C07K 14/805* (2013.01); *A61K 38/00* (2013.01)
USPC ............. 514/185; 514/2.3; 514/184; 540/145

(58) Field of Classification Search
None
See application file for complete search history.

(56) References Cited

U.S. PATENT DOCUMENTS

| 5,629,198 A * | 5/1997 | Mizumoto et al. ............ 435/262 |
| 6,001,808 A | 12/1999 | Bourinbaiar |
| 6,333,319 B1 | 12/2001 | Scherts et al. |

FOREIGN PATENT DOCUMENTS

| RU | 2193038 C2 | 11/2002 |
| RU | 2238950 C2 | 10/2004 |
| RU | 2250906 C2 | 4/2005 |
| RU | 2280649 C1 | 7/2006 |
| RU | 2296131 C2 | 3/2007 |
| RU | 2007125604 A | 1/2009 |

OTHER PUBLICATIONS

Machine translation of RU 2,280,649 (Sep. 2013).*
Machine translation of RU 2,250,906 (Sep. 2013).*
Machine translation of RU 2,238,950 (Sep. 2013).*
Machine translation of RU 2,296,131 (Sep. 2013).*
Amsterdam, D. ; (1996) "Susceptibility testing of antimicrobials in liquid media" ; Source—In Lorian, V., ed. Antibiotics in laboratory medicine, 4th ed. Williams and Wilkins, Baltimore, Maryland, pp. 52-111.
Antonenko, Y.N., et al. ; (2005) "Larege unselective pore in lipid bilayer membrane formed by positively charged peptides containing a sequence of gramicidin" ; Source—A//FEBS Letters, vol. 579, pp. 5247-5252.
Giuliani, A. et al. ; (2007) "Antimicrobial peptides: an overview of a promising class of therapeutics" ; Source—Central European Journal of Biology, vol. 2, No. 1, pp. 1-33.
Herrell and, W.E. & Heilman, D. ; (1941) "Experimental and Clinical Studies on Gramicidin" ; Source—J. Clin. Invest., vol. 20, pp. 583-591.
Kastin, A.J. ; (2006) "Handbook of Biologically Active Peptides" ; Source—Elsevier, Academic Press, USA, p. 576.
Nagamurthi, G. & Rambhav, S. ; (1985) "Gramicidin-S: Structure-Activity Relationship" ; Source—J. Biosci., vol. 7, No. 3-4, pp. 323-329.
Nitzan, Y. et al. ; (1987) "Characterization of Hemin Antibacterial Action on *Staphylococcus aureus*" ; Source—FEMS Microbiol. Lett., vol. 48, No. 3, pp. 401-406.

(Continued)

*Primary Examiner* — Theodore R West
(74) *Attorney, Agent, or Firm* — Banner & Witcoff, Ltd.

(57) ABSTRACT

The invention relates to novel antimicrobial, including antibacterial and antifungal, agents and compositions based on hemin derivatives of general formula (I), and also to the production of novel hemin derivatives. The advantages of antibacterial agents based on hemin derivatives are their biocompatibility, biodegradability, high effectiveness against resistant bacteria and widespread microfungi that are harmful to humans, and freedom from toxicity and side effects.

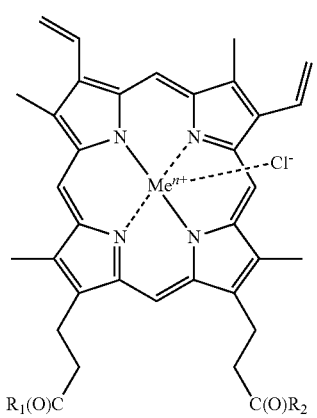

21 Claims, 3 Drawing Sheets

(56) References Cited

OTHER PUBLICATIONS

Xiao, J. et al. ; (2005) "Electrostatic versus Steric Effects in Peptidomimicry: Synthesis and Secondary Structure Analysis of Gramicidin S Analogues with (E)-Alkene Peptide Isosteres" ; Source—J. Am. Chem. Soc., vol. 127, No. 16, pp. 5742-5743.

Yarrow, D. ; (1998) "Methods for the Isoloation, Maintenance and Identification of Yeasts" ; Source—In: The Yeasts, A Taxonomic Study, Elsevier, Ed. by Kurtsman C.P., Fell J.W., pp. 77-100.

Zheltukhina, G.A. et al. ; (2006) Bioorg. Khim., vol. 32, No. 2, pp. 198-210 (Russian and English version of the article).

Stojiljkovic et al., "Antimicrobial Properties of Porphyrins", Expert Opinion on Investigational Drugs, Ashley Publications Ltd., London, GB, vol. 10, No. 2, (2001), pp. 309-332.

Supplemental European Search Report issued in corresponding European Application, Application No. EP 10815682, issued on Dec. 11, 2012.

Paeshuyse et al., "Hemin potentiates the anti-hepatitis C virus activity of the antimalarial drug artemisinin," Biochemical and Biophysical Research Communications, vol. 348, 2006, pp. 139-144.

Jianfeng et al., "Anti-anemic effect of hemin," Chinese Journal of Biochemical Pharmaceutics, 1997, vol. 18, No. 1, pp. 34-36.

* cited by examiner

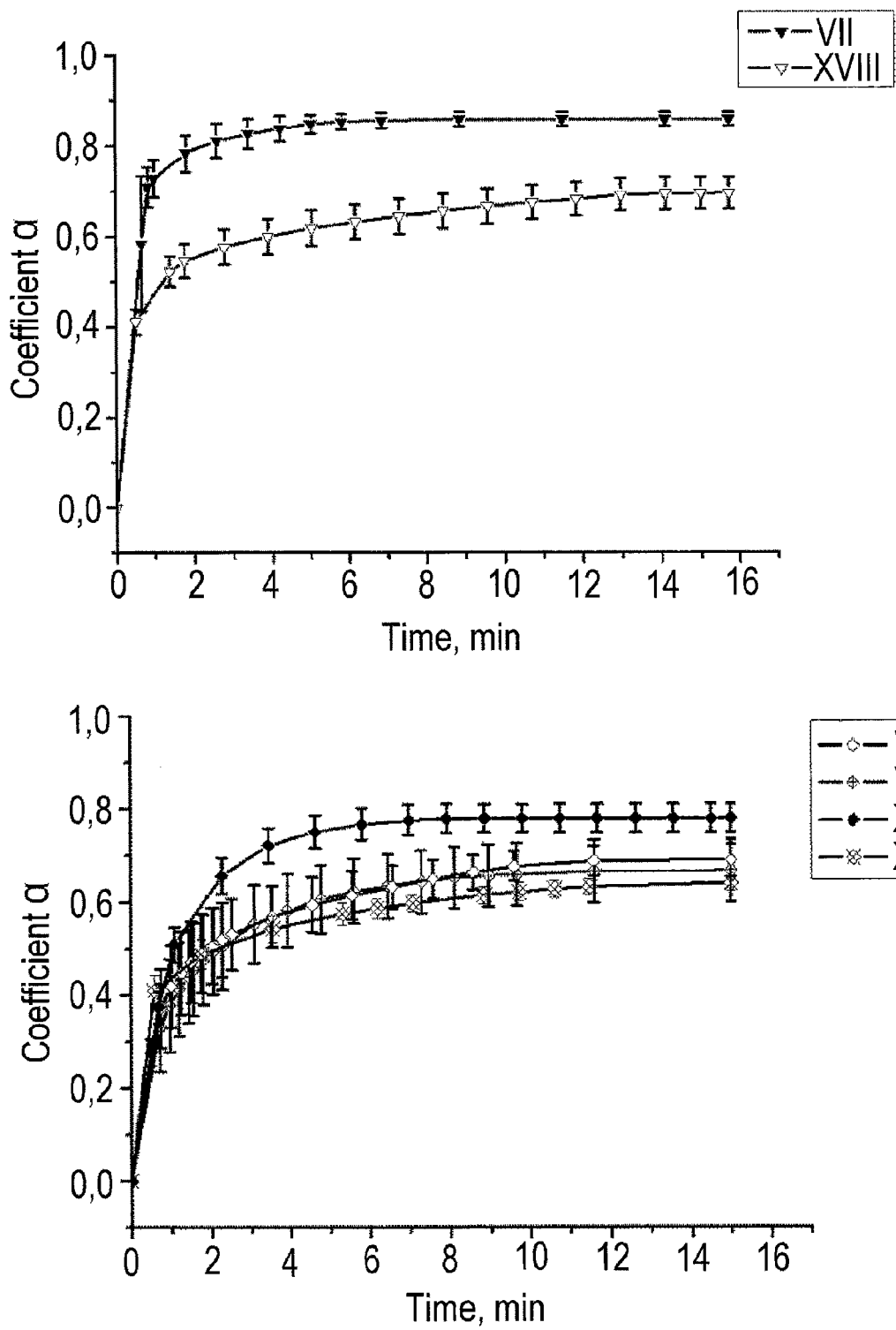
FIG.1 (Continue)

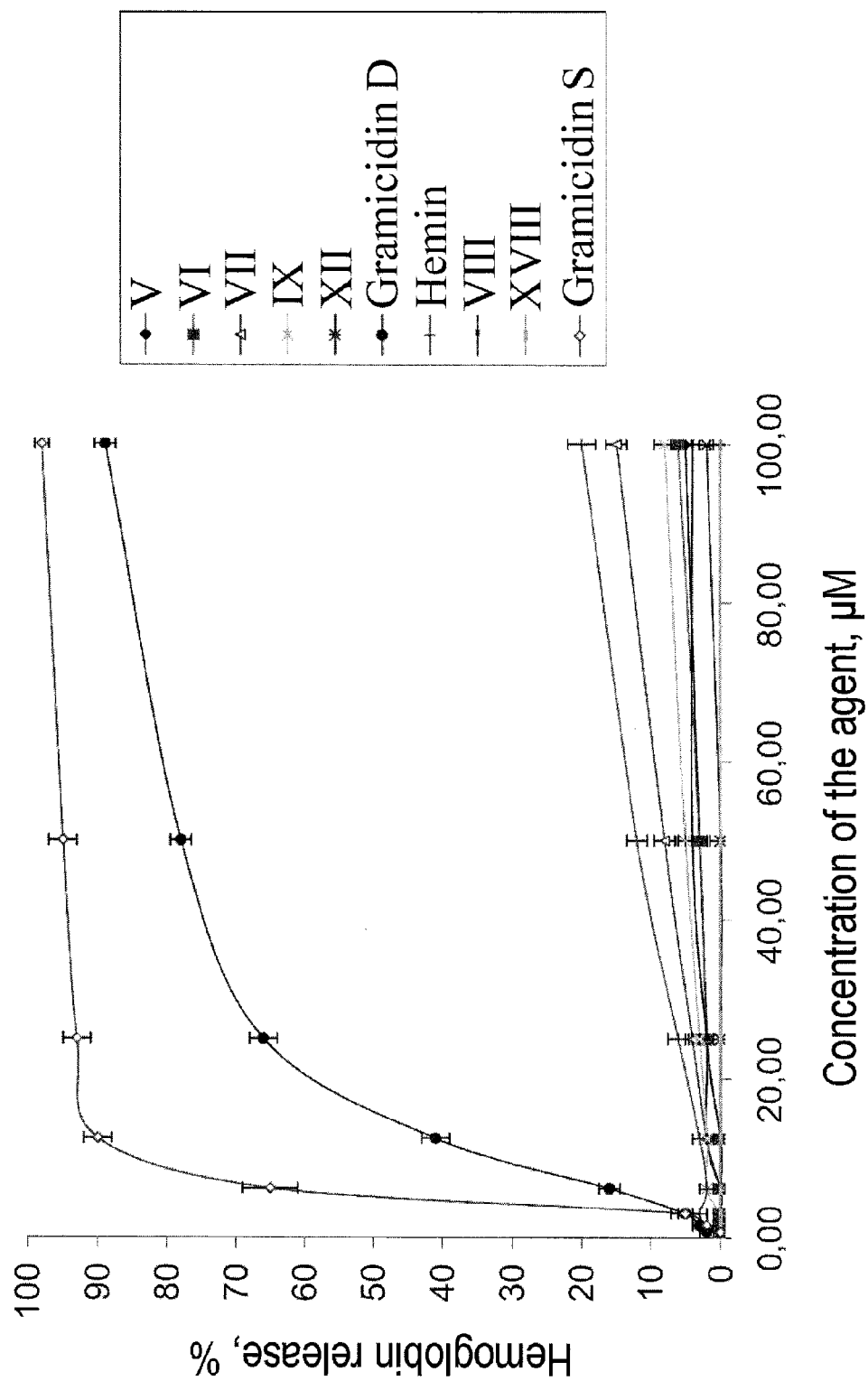

SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: peptide of hemin deriative

<400> SEQUENCE: 1

Arg Arg Trp His Arg Leu Lys Glu
 1               5

<210> SEQ ID NO 2
<211> LENGTH: 7
<212> TYPE: PRT
<213> ORGANISM: Artificial Sequence
<220> FEATURE:
<223> OTHER INFORMATION: peptide of hemin deriative

<400> SEQUENCE: 2

Arg Trp His Arg Leu Lys Glu
 1               5

<210> SEQ ID NO 3
<211> LENGTH: 17
<212> TYPE: PRT
<213> ORGANISM: Bacillus brevis
<220> FEATURE:
<221> NAME/KEY: VARIANT
<222> LOCATION: (1)...(17)
<223> OTHER INFORMATION: Xaa = Trp, Tyr, or Phe

<400> SEQUENCE: 3

Val Gly Ala Leu Ala Val Val Val Trp Leu Xaa Leu Trp Leu Trp Leu Trp
 1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: peptide of hemin deriative

<400> SEQUENCE: 4

Arg Arg Trp Trp Arg Phe
 1               5

ANTIMICROBIAL AGENTS BASED ON HEMIN DERIVATIVES

This application incorporates by reference the contents of a 1.15 kb text file created on Dec. 24, 2013 and named "13395149sequencelisting.txt," which is the sequence listing for this application.

CROSS-REFERENCE TO RELATED APPLICATIONS

This application is a U.S. National Stage application under 35 U.S.C. §371 of International Application PCT/RU2010/000488 (published as WO 2011/031187 A1), filed Sep. 8, 2010, which claims priority to Application RU 2009133914, filed Sep. 10, 2009. Benefit of the filing date of each of these prior applications is hereby claimed. Each of these prior applications is hereby incorporated by reference in its entirety.

TECHNICAL FIELD

The invention relates to the field of bioorganic chemistry and is directed to the development of novel antimicrobial agents and compositions of hemin derivatives and to the production of novel hemin derivatives.

BACKGROUND ART

Many dangerous diseases in humans and animals are known to be caused by microorganisms, such as bacteria and microfungi. Bacteria cause epidemic diseases such as cholera, typhoid fever, paratyphoid fever, plague, diphtheria, tularemia, brucellosis, as well as tuberculosis, septicemia (blood poisoning), leprosy, syphilis, and others. In animals, bacteria cause equinia, anthrax, tuberculosis, and other diseases. Fungal diseases mainly affect the skin and mucous membranes, particular examples being keratomycoses, microsporum, trichophytosis, and cryptococcosis.

Strategy in the fight against microorganisms involves the administration of antimicrobial agents, such as antibacterial agents (including antibiotics) and antifungal agents. However, many know agents suffer from drawbacks such as toxicity, sensitivity to proteolytic enzymes, a hemolytic effect, and an insufficient range of antimicrobial activity. In particular, bacteria rapidly develop resistance toward known antimicrobial agents, primarily antibiotics. In this context, a search for novel nontoxic and biocompatible antimicrobial agents that would not cause resistance is of great interest.

Hemin is known to have an antimicrobial activity against *Staphylococcus aureus* [Y. Nitzan, H. Ladan, S. Gozansky, and Z. Malik, "Characterization of Hemin Antibacterial Action on *Staphylococcus aureus*," FEMS Microbiol. Lett., 1987, Vol. 48 (3), pp. 401-406]. However, the use of hemin as an antibacterial agent is hampered by its water insolubility, hemolytic activity, and short-term antibacterial effect.

Attempts have been undertaken at modifying hemin by conjugating it with amino acids and peptides with the aim of designing biologically active derivatives. As a result of modifying the carboxy groups of hemin by preparing the corresponding amides, compounds of general formula (I) have been prepared and characterized, wherein $R_1$ and $R_2$, the same or different, are —OH or an amino acid or peptide moiety, and wherein $R_1$ and $R_2$ cannot simultaneously be —OH.

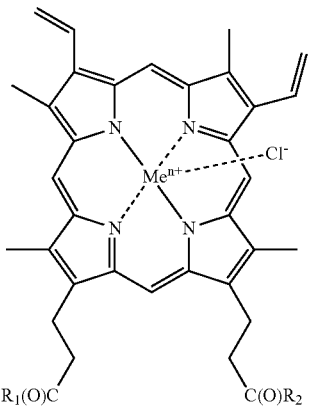

Some peptide hemin derivatives of general formula (I), in particular those wherein one of $R_1$ and $R_2$ is —OH and the other is -ArgArgTrpHisArgLeuLysGlu(OMe)OH (SEQ ID NO:1, compound V), or -ArgTrpHisArgLeuLysGlu(OMe)OH (SEQ ID NO:2, compound VI), have been found to have a nuclease (nucleolytic) activity, which is manifested as the ability to destroy plasmid DNA [RU patent No. 2250906, Apr. 27, 2005; Zheltukhina, G. A., Lobanova, T. N., Nebolsin, V. E., Gallyamov, M. O., Dranitsyna, S. M. and Kostanyan, I. A., Bioorg. Khim., 2006, Vol. 32, No. 2, pp. 198-210].

Some amino acid and peptide hemin derivatives of general formula (I), namely, those wherein one of $R_1$ and $R_2$ is —OH and the other is -ArgArgTrpHisArgLeuLysGlu(OMe)OH (SEQ ID NO:1 compound V), or $R_1=R_2=$-ArgOMe (compound VII), are capable of inhibiting HIV proteinase and, as a result, exert an anti-HIV antiviral action [RU patent No. 2238950, Oct. 27, 2004].

Antiviral activity has been demonstrated for some hemin derivatives of general formula (I), namely, for those wherein $R_1=R_2=$-SerOMe (compound VIII), $R_1=R_2=$-βAlaHis (compound X), $R_1=R_2=$-ArgOMe (compound VII), $R_1=R_2=$-βAlaHA (compound IX, HA=histamine moiety), or wherein one of $R_1$ and $R_2$ is —OH and the other is -ArgArgTrpHisArgLeuLysGlu(OMe)OH (SEQ ID NO:1, compound V), or -ArgTrpHisArgLeuLysGlu(OMe)OH (SEQ ID NO:2, compound VI) [RU application No. 2007125604, Jan. 20, 2009].

The antimicrobial (specifically, antibacterial and antifungal) activity of the aforementioned hemin derivatives is, however, not known in the art.

On the other hand, a lot of attention has recently been paid to the design of novel antimicrobial agents based on antimicrobial peptides (AMPs) [A. Giuliani, G Pirri, and S. F. Nicoletto, "Antimicrobial Peptides: An Overview of a Promising Class of Therapeutics," Central European Journal of Biology, 2007, Vol. 2 (1), pp. 1-33].

Of the known antimicrobial peptides, we can mention linear gramicidin D, which is a mixture of peptides of formula (II):

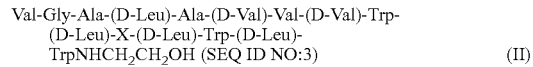

wherein X=Trp, Tyr, or Phe
[W. E. Herrell and D. Heilman, "Experimental and Clinical Studies on Gramicidin," J. Clin. Invest., 1941, Vol. 20, pp. 583-591]; and cyclic gramicidin S of formula (III):

[G Nagamurthi and S. Rambhav, "Gramicidin-S: Structure—Activity Relationship," J. Biosci., 1985, Vol. 7, Nos. 3-4, pp. 323-329].

Compound II is effective against Gram-positive bacteria [W. E. Herrell and D. Heilman, "Experimental and Clinical Studies on Gramicidin," J. Clin. Invest., 1941, Vol. 20, No 583] and against some viruses, in particular herpes virus [U.S. Pat. No. 6,001,808, 1999]. Compound III is effective primarily against Gram-positive bacteria in concentrations of 5 to 15 µM [Jingbo Xiao, Bernard Weisblum, and Peter Wipf, "Electrostatic versus Steric Effects in Peptidomimicry: Synthesis and Secondary Structure Analysis of Gramicidin S Analogues with (E)-Alkene Peptide Isosteres," J. Am. Chem. Soc., 2005, 127 (16), pp. 5742-5743]. Compounds II and III are used in medical practice only for topical applications. Drawbacks of these antimicrobial agents consist in their relatively long lengths and the associated relatively high costs; an insufficient range of antibacterial, antifungal, and antiviral effect; and side effects of their application, primarily hemolysis of erythrocytes and allergic reactions.

Further, there is an Arg-Gly-Asp peptide (IV), which is a fragment of cecropin family antimicrobial peptides, many microbial proteins, and mammal cell surface fibronectin [A. J. Kastin, "Handbook of Biologically Active Peptides," Elsevier/Academic Press, USA, 2006, p. 576]. However, its usefulness as an agent for the treatment of infectious diseases has not yet been studied.

The main obstacles to the use of AMPs in clinical practice consist of their relatively high costs, susceptibility to proteolytic enzymes, and the hemolytic effect intrinsic to many AMPs.

In addition, the major pathway to produce antimicrobial peptides is currently a solid-phase method, which makes them very expensive and their use uneconomical. Therefore, a search for shorter analogues of AMPs and their derivatives, in particular, for conjugates with compounds of other classes, is of great interest.

In the context of the persistent need for improving antimicrobial agents as regards reducing the toxicity and other side effects thereof and for enhancing their activity against resistant strains, hemin derivatives have been proposed for use as such the agents.

SUMMARY OF THE INVENTION

This invention relates to the use of hemin derivatives of general formula (I)

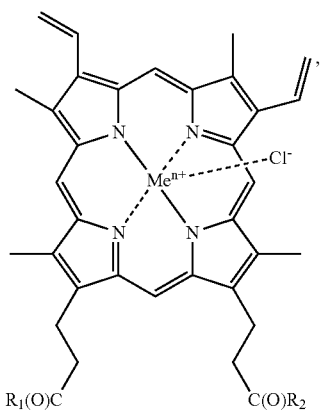

I wherein $R_1$ and $R_2$ are the same or different, provided that both of $R_1$ and $R_2$ are not simultaneously —OH, and wherein either one of $R_1$ and $R_2$ is —OH and the other is -ArgArgTrpHisArgLeuLysGlu(OMe)OH (SEQ ID NO: 1), -ArgTrpHisArgLeuLysGlu(OMe)OH (SEQ ID NO:2), -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), —N$^\delta$-cyclo-(Orn-Leu-D-Phe-Pro-Val)$_2$ (gramicidin S), -Arg-Gly-Asp-OH, or -Arg-Arg-Trp-Trp-Arg-Phe-OH (SEQ. ID NO:4);

or $R_1$ and $R_2$ are each -ArgOMe, -SerOMe, -βAlaHA, -βAlaHis, —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe, wherein HA is the histamine moiety

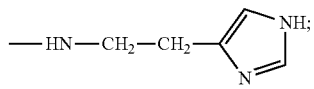

and Me$^{n+}$ is Fe$^{2+}$ or Fe$^{3+}$;

or isomers or mixtures of isomers thereof, or pharmaceutically acceptable salts thereof, as antimicrobial agents.

Further, the invention relates to an antimicrobial (in particular, antibacterial and/or antifungal) agent based on the aforementioned compounds of formula (I) and the corresponding pharmaceutical, antiseptic, and/or disinfectant compositions, and to a method for treating and/or preventing diseases caused by microorganisms.

Still further, the invention relates to novel hemin derivatives of general formula (I)

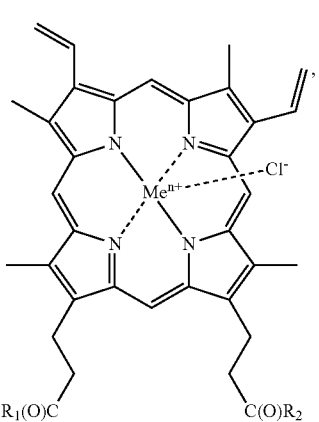

I wherein $R_1$ and $R_2$ are the same or different, provided that both of $R_1$ and $R_2$ are not simultaneously —OH, and wherein either one of $R_1$ and $R_2$ is —OH and the other is -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEC) ID NO:3, gramicidin D), —N$^\delta$-cyclo-(Orn-Leu-D-Phe-Pro-Val)$_2$ (gramicidin S), -Arg-Gly-Asp-OH, or -Arg-Arg-Trp-Trp-Arg-Phe-OH (SEQ ID NO:4);

or $R_1$ and $R_2$ are each —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe, wherein HA is the histamine moiety

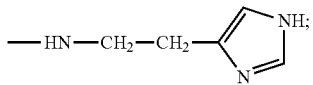

and $Me^{n+}$ is $Fe^{2+}$ or $Fe^{3+}$;
or isomers or mixtures of isomers thereof, or pharmaceutically acceptable salts thereof, and to a process for producing these compounds.

BRIEF DESCRIPTION OF DRAWINGS

FIG. 2 shows plots of the hemolytic activity (evaluated as the intensity of hemoglobin release from erythrocytes) versus concentration for hemin derivatives.

DETAILED DESCRIPTION OF THE INVENTION

Figure 1:
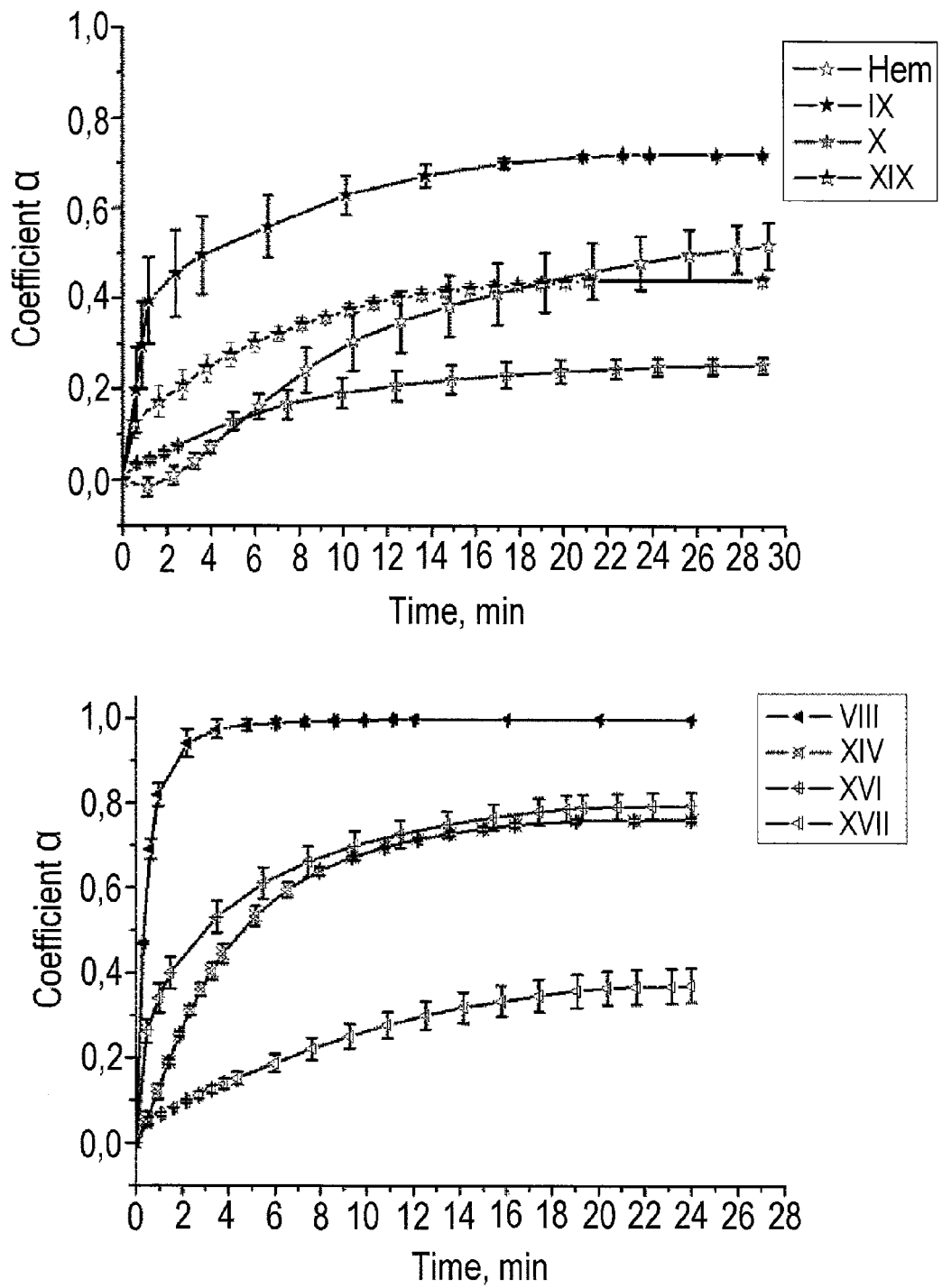
FIG. 1 shows plots of the dynamics of carboxyfluorescein release from model liposomes induced by hemin derivatives.

The inventors were surprised to discover that the compounds of the above formula (I), which represent hemin conjugates with peptides, amino acids, or analogues thereof, are promising antimicrobial agents.

The advantages of the hemin derivatives of formula (I) consist in their biocompatibility and biodegradability, low toxicity with respect to normal human cells, the absence of hemolytic effect, and a high antibacterial efficacy, in particular, against resistant strains, combined with an antifungal activity.

Without being intended to confine themselves to any particular theory, the inventors suggest that the antimicrobial effect of the compounds of formula (I) may partially arise from their destructive action on lipid membranes, this action known to be one of the major mechanisms of the antimicrobial effect. This action is demonstrated in Example 12 and FIG. 1.

Thus, the following novel compounds of formula (I) have been produced and studied:
Compound (XI): one of $R_1$ and $R_2$ is —OH and the other is -Arg-Gly-Asp-OH;
Compound (XII): one of $R_1$ and $R_2$ is —OH and the other is -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH,
wherein X=Trp, Phe, or Tyr, (SEQ ID NO:3, gramicidin D);
Compound (XIII): one of $R_1$ and $R_2$ is —OH and the other is —N$^\delta$-cyclo-(Orn-Leu-D-Phe-Pro-Val)$_2$ (gramicidin S);
Compound (XIV): $R_1$=$R_2$=—NHCH$_2$CH$_2$OH;
Compound (XV): $R_1$=$R_2$=-GlyOMe;
Compound (XVI): $R_1$=$R_2$=—NHCH(CH$_2$OH)CH$_2$OH;
Compound (XVII): $R_1$=$R_2$=—NHCH$_2$CH(OH)CH$_2$OH;
Compound (XVIII): $R_1$=$R_2$=-Glu(ArgOMe)-ArgOMe;
Compound (XIX): $R_1$=$R_2$=-HA;
Compound (XX): one of $R_1$ and $R_2$ is —OH and the other is -Arg-Arg-Trp-Trp-Arg-Phe-OH (SEQ ID NO:4); and
Compound (XXI): $R_1$=$R_2$=-Arg-ArgOMe;
wherein HA is

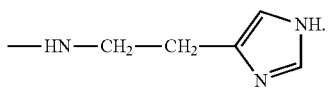

Apart from the aforementioned novel compounds, some known hemin derivatives of general formula (I) have been studied and found to demonstrate similar properties, namely:
Compound (V): one of $R_1$ and $R_2$ is —OH and the other is -ArgArgTrpHisArgLeuLysGlu(OMe)OH (SEQ ID NO: 1);
Compound (VI): one of $R_1$ and $R_2$ is —OH and the other is -ArgTrpHisArgLeuLysGlu(OMe)OH (SEQ ID NO:2);
Compound (VII): $R_1$=$R_2$=-ArgOMe;
Compound (VIII): $R_1$=$R_2$=-SerOMe;
Compound (IX): $R_1$=$R_2$=-βAlaHA, wherein HA- is the histamine moiety; and
Compound (X): $R_1$=$R_2$=-βAlaHis;

Compounds (V) and (VI) are disclosed in the RU patent No. 2250906, Apr. 27, 2005 and the article by Zheltukhina, G. A., Lobanova, T. N., Nebolsin, V. E., Gallyamov, M. O., Dranitsyna, S. M., and Kostanyan, I. A., Bioorg. Khim., 2006, Vol. 32, No. 2, pp. 198-210; compound (VII) is disclosed in the RU patent No. 2238950, Oct. 27, 2004; and compounds (VIII), (IX), and (X) are disclosed in the RU application No. 2007125604, Jan. 20, 2009. However, the antimicrobial (in particular, antibacterial or antifungal) activity of these compounds has not yet been studied.

Thus, this invention is directed to the use of hemin derivatives of general formula (I)

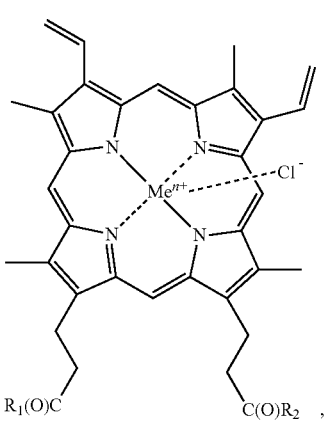

I wherein $R_1$ and $R_2$ are the same or different, provided that both of $R_1$ and $R_2$ are not simultaneously —OH, and wherein
either one of $R_1$ and $R_2$ is —OH and the other is -ArgArgTrpHisArgLeuLysGlu(OMe)OH (SEQ ID NO: 1), -ArgTrpHisArgLeuLysGlu(OMe)OH (SEQ ID NO:2), -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), —N$^\delta$-cyclo-(Orn-Leu-D-Phe-Pro-Val)$_2$ (gramicidin S), -Arg-Gly-Asp-OH or -Arg-Arg-Trp-Trp-Arg-Phe-OH (SEQ ID NO:4);
or $R_1$ and $R_2$ are each -ArgOMe, -SerOMe, -βAlaHA, -βAlaHis, —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe,
wherein HA is the histamine moiety

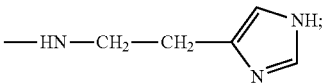

and $Me^{n+}$ is $Fe^{2+}$ or $Fe^{3+}$;

or isomers or mixtures of isomers thereof, or pharmaceutically acceptable salts thereof, as antimicrobial agents.

Antimicrobial activity comprises both antibacterial and antifungal activities.

The above-described compounds of formula (I) are active against Gram-positive bacteria, such as *Staphylococcus* (e.g., *Staphylococcus aureus*), *Bacillus* (e.g., *Bacillus subtilis*), *Enterococcus* (e.g., *Enterococcus faecalis*), and *Micrococcus* (e.g., *Micrococcus luteus*) bacterial genera, in particular, against bacteria that are resistant to known antibacterial agents. Preferably, the above-listed bacteria are *Bacillus subtilis* BKM B-501, *Staphylococcus aureus* 209P, *Enterococcus faecalis* BKM B-871, or *Micrococcus luteus* BKM Ac-2230 strains. Still more preferably, the aforementioned compounds have antibacterial activity against *Staphylococcus aureus* No. 25923 ATCC, *Staphylococcus aureus* No. 100 KC, *Staphylococcus epidermidis* No. 533, *Enterococcus faecalis* No. 559, or *Enterococcus faecium* No. 569 resistant strains.

Furthermore, the above-described compounds of formula (I) are active against *Cryptococcus* microfungi (in particular, *Cryptococcus neoformans*, preferably the *Cryptococcus neoformans* No. 3465 strain) and *Candida* microfungi (in particular, *Candida albicans*, preferably the *Candida albicans* No. 927 strain).

The compounds of formula (I) can exist as isomers or mixtures of isomers, which are fully covered by the scope of the claimed invention. For example, if one of the two carboxy groups of hemin is modified, a mixture of (6) and (7) derivatives can be formed.

All amino acids in the hemin derivatives are L-amino acids unless specified otherwise.

The compounds of formula (I) can be used either in the form of salts with pharmaceutically acceptable acids (e.g., lactic, tartaric, citric, hydrochloric, or another acid), or in the form of salts of their carboxy groups with alkali or alkaline-earth metal ions (such as sodium, potassium, and calcium) or with, for example, pharmaceutically acceptable bases (such as ammonia and ethanolamine).

The aforementioned compounds of formula (I) and/or salts thereof can be used as active ingredients of pharmaceutical compositions (e.g., in solid, semisolid, or liquid forms) formulated with an organic or inorganic carrier or excipient.

The active ingredient in the composition can be formulated with conventional nontoxic and pharmaceutically acceptable carriers that are suitable for preparing solutions, tablets, pills, capsules, suppositories, emulsions, suspensions, sprays, inhalers, drops, ointments, or other dosage forms. Carriers can be water, glucose, lactose, gum arabic, gelatin, starch, magnesium trixylitol, talc, cornstarch, urea, polyethylene glycol, and other carriers suitable for manufacturing solid, soft, or liquid preparations. Herein, stabilizers, thickeners, coloring agents, and flavoring agents may be used as additives.

A compound of formula (I) is contained in the composition in an amount sufficient for providing the antimicrobial effect.

In manufacturing a unit dosage form, the amount of the active ingredient formulated with a carrier can be varied depending on the recipient of therapy and on the particular route of administration of the therapeutic agent.

For example, when compounds of the present invention are used as solutions for injection, the content of the active principle in the solution ranges from 0.001 to 1% by weight. Diluents for the compounds can be 0.9% sodium chloride solution, distilled water, Novocain solution for injections, Ringer's solution, and glucose solution. When compounds of general formula (I) are used as tablets or suppositories, the amount of the compound ranges from 1.0 to 100.0 mg per unit dosage form. For tablets and suppositories, the pharmaceutical excipient can be any pharmaceutically suitable base.

Inasmuch as compounds of general formula (I) are both water-soluble and lipophilic, they can be used as aqueous solutions, alcoholic solutions, ointments, creams, etc.

Further, the invention relates to an antimicrobial therapeutic agent based on the aforementioned compounds of formula (I) and to a method for treating diseases caused by the aforementioned bacteria and/or microfungi, this method comprising administering to a patient in need thereof said compound of formula (I) or a pharmaceutical composition thereof.

The method is intended for treating mammal patients, in particular humans. The recommended doses of a compound of formula (I) are from 0.01 to 10 mg/kg.

Inasmuch as compounds of formula (I) have antibacterial and antifungal activities, they can likewise be used as (or in) antiseptic and/or disinfectant agents. These agents can be prepared as, for example, solutions with diverse solvents, such as water and lower alcohols (e.g., 1-propanol or 2-propanol).

Another subject matter of the invention consists of novel hemin derivatives of general formula (I)

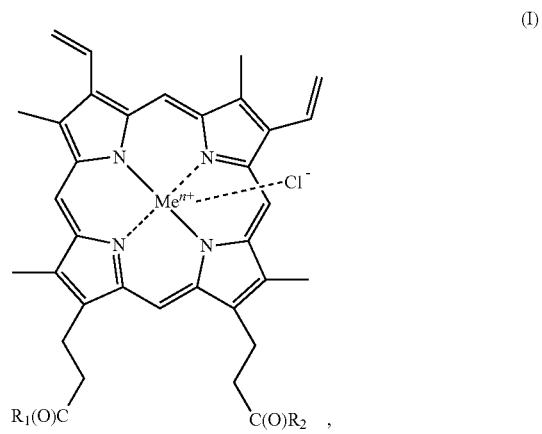

(I)

wherein $R_1$ and $R_2$ are the same or different, provided that both of $R_1$ and $R_2$ are not simultaneously —OH, and wherein either one of $R_1$ and $R_2$ is —OH and the other is -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), —N$^\delta$-cyclo-(Orn-Leu-D-Phe-Pro-Val)$_2$ (gramicidin S), -Arg-Gly-Asp-OH, or -Arg-Arg-Trp-Trp-Arg-Phe-OH (SEQ ID NO:4);

or $R_1$ and $R_2$ are each —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe, wherein HA is the histamine moiety

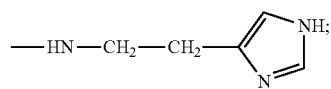

and Me$^{n+}$ is Fe$^{2+}$ or Fe$^{3+}$;

or isomers or mixtures of isomers thereof, or pharmaceutically acceptable salts thereof.

One more aspect of the invention relates to a process for producing the above-described novel compounds of formula (I).

Compounds of formula (I) are produced by reacting a hemin derivative activated at carboxy group(s) with an amino component.

Amino components can be peptides, amino acids (mostly, a-amino acids), or analogues thereof, in particular, Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), cyclo-(Orn-Leu-D-Phe-Pro-Val)$_2$ (gramicidin S), Arg-Gly-Asp-OH, NH$_2$CH$_2$CH$_2$OH, GlyOMe, NH$_2$CH(CH$_2$OH)CH$_2$OH, —NH$_2$CH$_2$CH(OH)CH$_2$OH, Glu(ArgOMe)-ArgOMe, histamine (HA), Arg-Arg-Trp-Trp-Arg-Phe-OH (SEQ ID NO:4), and Arg-ArgOMe.

Preferably, the amino groups of amino components (e.g., the α-amino groups of amino acids) are acylated with hemin bis-N-oxysuccinimide ester; or, for preparing monohemin derivatives, with hemin 6(7)-mono-N-oxy-5-norbornene-2,3-dicarboximide ester; or with a hemin derivative activated at one carboxy group, wherein the activating agent is di-tert-butyl pyrocarbonate in the presence of pyridine. The reactions are carried out in DMF for 0.5 to 2 h at a temperature of from −15° to +30° C.

Thus, what we claim are novel efficacious antimicrobial agents with antibacterial and antifungal activity based on hemin derivatives. Their advantages consist in biocompatibility, biodegradability, activity against resistant bacterial strains, non-toxicity, and freedom from side effects. Furthermore, the concentrations in which the claimed compounds are toxic for normal cells exceed their MICs (minimal inhibitory concentrations) and MBCs (minimal bactericidal concentrations) by two to three orders of magnitude. Therefore, it is highly probable that the claimed compounds have a wide range of antimicrobial activity, which renders them promising for use as therapeutic agents.

Further, the invention will be illustrated by examples that are in no means intended to limit the scope thereof.

NOTATIONS

DCC=N,N'-dicyclohexylcarbodiimide
DMSO=dimethyl sulfoxide
DOPC=dioleoylphosphatidylcholin
GrD=gramicidin D
HA=histamine
Hem=hemin moiety
MeOH=methanol
MES=2-(N-morpholino)ethanesulfonic acid
MH=Mueller-Hilton medium
OMe=methyl ether
ONb=N-oxy-5-norbornene-2,3-dicarboximide ester
O$^t$Bu=tert-butyl ether
Z=carbobenzoxy group
DMSO=dimethylsulfoxide
DMF=N,N'-dimethylformamide
IR=infrared spectroscopy
GI=growth inhibition
CF=carboxyfluorescein
MBC=minimal bactericidal concentration
MIC=minimal inhibitory concentration
MSC=minimal suppressing concentration
RP-HPLC=reversed-phase high performance liquid chromatography
Tris=tris(hydroxymethyl)aminomethane
TLC=thin-layer chromatography
CLF=chloroform
EA=ethyl acetate All quantities expressed in percent are percent by weight unless specified otherwise.

EXAMPLES

The reagents used were: L-amino acids and their derivatives purchased from Bachem (Germany) and Reanal (Hungary); DOPC (from Sigma-Aldrich); carboxyfluorescein (Fluka, Germany); MES (Sigma-Aldrich); Tris (Sigma-Aldrich); gramicidin D (Sigma-Aldrich); gramicidin S (Kraspharma, Russia); and analytical reagent grade (the Russian standard) potassium chloride (Khimmed, Russia).

All solvents were anhydrous, except for those used for extraction from aqueous solutions. The identity of the prepared compounds was verified by TLC on Kieselgel 60 F$_{254}$ plates (Merck, Germany) in the following systems: (1) chloroform-methanol (9:1), (2) chloroform-methanol (8:2), (3) chloroform-methanol (5:3), (4) chloroform-methanol-acetic acid (5:3:1), (5) methanol-acetic acid-water (4:1:1), and (6) butanol-acetic acid-water (4:1:1). Chromatograms were developed with the chlorine-tolidine reagent, ninhydrin, or by fluorescence in the UV.

High-resolution mass spectra were obtained on an Ultraflex (Bruker, Germany) time-of-flight mass spectrometer using matrix-assisted laser desorption/ionization (TOF MALDI); 2,5-dihydroxybenzoic acid matrices were used.

IR spectra were recorded on a Magna 750 (Nicolet, USA) Fourier-transform spectrometer.

Electronic spectra were recorded on a Jasco model UV/VS 7800 (Japan) spectrophotometer.

RP-HPLC was carried out on a Gilson 305 (Gilson, France) instrument.

Preparative RP-HPLC was carried out on a Luna 10μ column, C5 reversed phase, 250×21.2 mm (Phenomenex, USA) under the following conditions:

isocratic elution with a 0.1% TFA solution in water and a flow rate of 4 mL/min. Absorption was recorded at a wavelength of 220 nm (7).

The dynamics of CF release from liposomes was monitored on a Cary Eclipse (Varian, USA) fluorimeter.

Liposomes were obtained with an Avanti (Avanti Polar Lipids, USA) mini-extruder.

Example 1

6,7-Bis(N$^α$-Glycyl Methyl Ester)-Protohemin IX (Compound XI; R$_1$=R$_2$=-GlyOMe)

To a suspension of 0.030 g (0.236 mmol) of H-GlyOMe-.HCl in 1.5 mL DMF 0.033 mL (0.236 mmol) of Et$_3$N was added and stirred at room temperature for 3 min.

To the resulting solution, a solution of 0.100 g (0.118 mmol) of protohemin IX 6,7-bis-N-oxysuccinimide ester (I) in 5 mL DMF was added and stirred for 2 h at room temperature. The reaction was monitored by TLC under conditions (1) and (2). The solution was concentrated to 0.5 mL under vacuum, and 6 mL of diethyl ether was added. The resulting residue was dissolved in CLF to precipitate Et$_3$N.HCl white crystals, and the solution was decanted to get rid of them. The solvent was removed under vacuum. To introduce Cl$^−$ counterions, the residue was dissolved in 15 mL of CLF-MeOH (8:2), shaken two times with 7.5 mL of 0.5 N hydrochloric acid, and washed with water to a neutral reaction. The solvent was removed under vacuum. The substance was purified on a column (20×2 cm) packed with Kieselgel 60 F$_{254}$ silica gel (Merck, Germany); the eluent was CLF-MeOH (8:2). The fraction containing the substance with Rf of 0.71 (2) was collected. The solvent was removed under vacuum. Yield: 0.063 g (67%); Rf: 0.26 (1), 0.71 (2). Electronic spectrum, $\lambda_{max}$, nm, CLF:MeOH (8:2), ($\epsilon \times 10^{-3}$): 400 (115.9), 508 (9.38), 640 (3.81). FT-IR spectrum, $\nu$, cm$^{-1}$, KBr pellet: 1737 (CO est.), 1648 (amide I), 1539 (amide II). Mass spectrum, m/z: [M]$^+$ 758.5.

Example 2

6,7-bis-Histaminyl-Protohemin IX (Compound XIX, $R_1=R_2=HA$)

To a solution of 0.026 g (0.236 mmol) of histamine in 1.5 mL DMF added was a solution of 0.100 g (0.118 mmol) of protohemin IX 6,7-bis-N-oxysuccinimide ester (I) in 4 mL DMF and stirred for 20 min at room temperature. The reaction was monitored by TLC under conditions (2) and (3). The solution was concentrated to 1 mL under vacuum, and 10 mL of diethyl ether was added. To introduce Cl$^-$ counterions, the residue was dissolved in 4 mL MeOH, and 0.093 mL (0.354 mmol) of 3.8 N HCl/MeOH was added to adjust pH to 4. The solvent was removed under vacuum at 30° C. The substance was purified on a column (31×2 cm) packed with Kieselgel 60 $F_{254}$ silica gel (Merck, Germany); the eluent was CLF-MeOH (5:3). The fraction containing the substance with Rf of 0.64 (3) was collected. The solvent was removed under vacuum. Yield: 0.049 g (51%); Rf: 0.25 (2), 0.64 (3). Electronic spectrum, $\lambda_{max}$, nm, CLF:MeOH (8:2), ($\epsilon \times 10^{-3}$): 388 (49.1), 508 (4.18), 640 (1.76). FT-IR spectrum, $\nu$, cm$^{-1}$, KBr pellet: 1644 (amide I), 1543 (amide II). Mass spectrum, m/z: [M]$^+$ 802.3.

Example 3

6,7-bis[bis(N$^\alpha$-L-Arginyl Methyl Ester)-L-Glutamyl]-Protohemin IX (Compound XVIII, $R_1=R_2=$-Glu(ArgOMe)-ArgOMe)

(1) Bis(N$^\alpha$-Arginyl Methyl Ester)-L-Glutamic Acid Dihydrochloride

To a suspension of 0.069 g (0.266 mmol) of H-ArgOMe.2HCl in 2 mL DMF added was 0.074 mL (0.531 mmol) of Et$_3$N and stirred at room temperature for 5 min. To the resulting solution added was 0.077 g (0.133 mmol) of Boc-glutamic acid bis(pentafluorophenyl) ester (which had been prepared beforehand) and stirred for 4 h at room temperature. The reaction was monitored by TLC under conditions (5). The solution was concentrated to 1 mL under vacuum, and 10 mL of diethyl ether was added. An oily precipitate was separated from the solvent by decantation, and the residual solvent was removed under vacuum. The substance was purified on a column (23×1 cm) packed with Kieselgel 60 $F_{254}$ silica gel (Merck, Germany); the eluent was methanol-acetic acid-water (4:0.5:0.5). The fraction containing the substance with Rf of 0.67 (5) was collected. The solvent was removed under vacuum. Yield: 0.073 g (77%); Rf: 0.67 (5). $[\alpha]_D^{25}$-8.53° (C., 0.38; MeOH). FT-IR spectrum, $\nu$, cm$^{-1}$, KBr pellet: 1735 (CO est.), 1653 (amide I), 1542, 1558 (amide II). Mass spectrum, m/z: [M]$^+$ 588.31.

To 0.073 g (0.0946 mmol) of bis(N$^\alpha$-arginyl methyl ester)-Boc-L-glutamic acid (V), poured was 6 mL of ~3 N HCl/MeOH. The resulting suspension was stirred for 2 h at room temperature. The process was monitored by TLC under conditions (6). After full conversion to the amino-unprotected dipeptide was reached, the solvent was removed under vacuum at 30° C. An oily residue was crystallized under anhydrous diethyl ether; the solvent was separated by decantation.

(2) 6,7-bis[(N$^\alpha$-L-Arginyl bis-Methyl Ester)-L-Glutamyl]-Protohemin IX (Compound XVIII)

To a suspension of the prepared H-Glu(ArgOMe)$_2$.3HCl in 1.5 mL DMF added was 0.047 mL (0.335 mmol) of Et$_3$N and stirred at room temperature for 2 min. Et$_3$N.HCl precipitation was observed. To the resulting suspension added was a solution of 0.047 g (0.0558 mmol) of protohemin IX 6,7-bis-N-oxysuccinimide ester (I) in 2 mL DMF and stirred for 22 h at room temperature. The reaction was monitored by TLC under conditions (6). The solution was concentrated to 1 mL under vacuum, and 10 mL of diethyl ether was added. To introduce Cl$^-$ counterions the residue was dissolved in 4 mL MeOH, and 3.8 N HCl/MeOH was added to adjust pH to 4. The solvent was removed under vacuum at 30° C. The substance was purified three times on a column (13×1 cm) packed with Sephadex LH-20; the eluent was MeOH. The fraction containing the substance with Rf of 0.07 (6) was collected. The solvent was removed under vacuum. Yield: 0.030 g (34%); Rf: 0.07 (6); Rf$_{(alumina)}$: 0.70 (6). Electronic spectrum, $\lambda_{max}$, nm, CLF:MeOH (8:2), ($\epsilon \times 10^{-3}$): 400 (92.2), 508 (6.31), 636 (2.39). FT-IR spectrum, $\nu$, cm$^{-1}$, KBr pellet: 1737 (CO est.), 1649 (amide I), 1528 (amide II). Mass spectrum, m/z: [M]$^+$ 1554.97.

Example 4

Protohemin IX 6,7-bis-N-(2-Hydroxyethyl)amide (Compound XIV, $R_1=R_2=$—NH—CH$_2$—CH$_2$—OH)

To a solution of 0.050 g (0.0591 mmol) of protohemin IX 6,7-bis-N-oxysuccinimide ester (I) in 3 mL DMF added was 0.010 mL (0.118 mmol) of aminoethanol and stirred for 20 min at room temperature. The reaction was monitored by TLC under conditions (2) and (3). The solution was concentrated to 1 mL under vacuum, and 10 mL of diethyl ether was added. To introduce Cl$^-$ counterions the residue was dissolved in 3 mL MeOH, and 3.8 N HCl/MeOH was added to adjust pH to 4. The solvent was removed under vacuum at 30° C. The substance was purified on a column (24×1 cm) packed with Kieselgel 60 $F_{254}$ silica gel (Merck, Germany); the eluent was CLF-MeOH (5:3). The fraction containing the substance with Rf of 0.52 (3) was collected. The solvent was removed under vacuum. Yield: 0.036 g (82.5%); Rf: 0.35 (2), 0.52 (3). Electronic spectrum, $\lambda_{max}$, nm, CLF:MeOH (8:2), ($\epsilon \times 10^{-3}$): 400 (183.0), 508 (5.23), 640 (2.08). FT-IR spectrum, $\nu$, cm$^{-1}$, KBr pellet: 1632 (amide I), 1549 (amide II). Mass spectrum, m/z: [M]$^+$ 702.5.

Example 5

Protohemin IX 6,7-bis-N-(1,3-Dihydroxypropan-2-yl)amide (Compound XVI, $R_1=R_2=$—HN—CH(CH$_2$OH)—CH$_2$OH)

To a solution of 0.050 g (0.0591 mmol) of protohemin IX 6,7-bis-N-oxysuccinimide ester (I) in 3 mL DMF added was a solution of 0.012 g (0.118 mmol) of 2-amino-1,3-propanediol in 0.5 mL DMF and stirred for 20 min at room temperature. The reaction was monitored by TLC under conditions (4). The solution was concentrated to 0.5 mL under vacuum, and 6 mL of diethyl ether was added. To introduce Cl$^-$ counterions the residue was dissolved in 9 mL of CLF- MeOH (8:2), shaken once with 4 mL of NaCl-saturated 0.06 N hydrochloric acid, and washed with water to a neutral reaction. The solvent was removed under vacuum. The substance was purified on a column (21×2 cm) packed with Sephadex LH-20; the eluent was MeOH. The fraction containing the substance with Rf of 0.56 (4) was collected. The solvent was removed under vacuum. Yield: 0.018 g (36%); Rf: 0.56 (4). Electronic spectrum, $\lambda_{max}$, nm, CLF:MeOH (8:2), ($\epsilon \times 10^{-3}$): 400 (40.5), 508 (2.68), 640 (1.02). FT-IR spectrum, $\nu$, cm$^{-1}$, KBr pellet: 1629 (amide I), 1550 (amide II). Mass spectrum, m/z: [M]$^+$ 762.0.

Example 6

Protohemin IX 6,7-bis-N-(2,3-Dihydroxypropyl) amide (Compound XVII, $R_1=R_2=$—HN—H$_2$C—CH(OH)—CH$_2$OH)

To a solution of 0.050 g (0.0591 mmol) of protohemin IX 6,7-bis-N-oxysuccinimide ester (I) in 3 mL DMF added was 0.009 mL (0.118 mmol) of 3-amino-1,2-propanediol and stirred for 20 min at room temperature. The reaction was monitored by TLC under conditions (3) and (4). The solution was concentrated to 0.5 mL under vacuum, and 6 mL of diethyl ether was added. To introduce Cl$^-$ counterions the residue was dissolved in 3 mL MeOH, and 3.8 N HCl/MeOH was added to adjust pH to 4. The solvent was removed under vacuum at 30° C. The substance was purified on a column (30×2 cm) packed with Kieselgel 60 F$_{254}$ silica gel (Merck, Germany); the eluent was CLF-MeOH:AcOH (5:3:0.5). The fraction containing the substance with Rf of 0.69 (4) was collected. The solvent was removed under vacuum. Yield: 0.023 g (46%); Rf: 0.33 (3), 0.69 (4). Electronic spectrum, $\lambda_{max}$, nm, CLF:MeOH (8:2), ($\epsilon \times 10^{-3}$): 396-400 (24.2), 488 (2.14), 600 (1.40). FT-IR spectrum, $\nu$, cm$^{-1}$, KBr pellet: 1634 (amide I), 1565 (amide II). Mass spectrum, m/z: [M]$^+$ 762.0.

Example 7

Protohemin IX 6(7)-Mono(-Val-Gly-Ala-D-Leu-Ala-D-Val-Val-D-Val-Trp-D-Leu-X-D-Leu-Trp-D-Leu-Trp-NH—CH$_2$CH$_2$OH)amide (SEQ ID NO:3, Compound XII, wherein one of $R_1$ and $R_2$ is —OH and the Other is -Val-Gly-Ala-D-Leu-Ala-D-Val-Val-D-Val-Trp-D-Leu-X-D-Leu-Trp-D-Leu-Trp-NH—CH$_2$CH$_2$OH, wherein X=Trp, Tyr, Phe; (SEQ ID NO:3)

To a solution of 32 mg (0.017 mmol) of gramicidin D in 0.650 mL of dry DMF, added was 48 µL of 1 N HCl in methanol. The reaction mixture was stirred for 72 h in the dark at room temperature. The solvent was removed under vacuum at 30° C. Yield: 30 mg (98%). Mass spectrum, m/z: [M]$^+$ 1854.0

To a solution of 30 mg (0.016 mmol) of deformylated gramicidin D in 0.2 mL DMF, added was 13.2 mg (0.016 mmol) of hemin 6(7)-mono-N-oxy-5-norbornene-2,3-dicarboximide ester and stirred for 1.5 h at room temperature. The solvent was removed under vacuum at 30° C. The residue was dissolved in chloroform. The residue was purified on a column (30×2 cm) packed with Kieselgel 60 F$_{254}$ silica gel (Merck, Germany); the eluent was CLF-MeOH (9:1). Yield: 23.5 mg (59%). FT-IR spectrum, $\nu$, cm$^{-1}$, KBr pellet: 1634 (amide I), 1565 (amide II). Rf: 0.65 (1).

Example 8

Protohemin IX 6(7)-Mono[Cyclo(Orn-Leu-D-Phe-Pro-Val)$_2$])amide (Compound XIII, wherein one of $R_1$ and $R_2$ is —OH and the other is —N$^\delta$-[cyclo-(Orn-Leu-D-Phe-Pro-Val)$_2$])

To a solution of 50 mg (0.077 mmol) of hemin in 0.5 mL of dry DMF, added were 1 mL of pyridine and 25.3 mg (0.116 mmol) of di-tert-butyl pyrocarbonate and stirred for 15 min at room temperature. Simultaneously to a suspension of 93.5 mg (0.077 mmol) of gramicidin S dihydrochloride in 0.5 mL DMF, added was 22 µL (0.154 mmol) of triethylamine and stirred for 2 min.

To the resulting mixed hemin anhydride, added was a solution of amino-unprotected gramicidin S and stirred for 3 h. The solvent was removed under vacuum at 30° C. The residue was dissolved in chloroform. The residue was purified on a column (30×2 cm) packed with Kieselgel 60 F$_{254}$ silica gel (Merck, Germany); the eluent was CLF-MeOH (12:1). Yield: 20 mg (15%). Mass spectrum, m/z: [M]$^+$ 1739.5. Electronic spectrum, $\lambda_{max}$, nm, chloroform:methanol (4:1), ($6 \times 10^{-3}$): 400 (105), 492 (10.6), 640 (6).

Example 9

6(7)-Mono(Arg-Gly-Asp)-Protohemin IX (Compound XI, wherein one of $R_1$ and $R_2$ is —OH and the other is -Arg-Gly-Asp-OH)

To a suspension of 20 mg (0.038 mmol) of Arg-Gly-Asp.CH$_3$COOH.CF$_3$COOH in 0.5 mL DMF added was 5 µL (0.038 mmol) of triethylamine and stirred for 2 min. Then, 62 µL (0.251 mmol) of bis-(O,N-trimethylsilyl)acetamide was added and stirred at room temperature for 30 min To the resulting suspension added was 32 mg (0.038 mmol) of protohemin IX 6,7-bis-N-oxysuccinimide ester, and the reaction mixture was stirred for 6 h. Then, the solvent was removed under vacuum, and the precipitate was dissolved in methanol to desilylate the carboxy groups of the tripeptide. The target product was crystallized from methanol. Yield: 20 mg (54%). Mass spectrum, m/z: [M]$^+$981.3.

Example 10

N$^\alpha$-[6(7)-(Protohemin IX)-yl]-ArgArgTrpTrpArgPhe-OH (SEQ ID NO:4, Compound XX, Wherein One of $R_1$ and $R_2$ is —OH and the Other is -ArgArgTrpTrpArgPhe-OH; SEQ ID NO:4)

(a) Solid-Phase Synthesis of ArgArgTrpTrpArgPhe-OH (SEQ ID NO:4, Compound XXI) on 2-Chlorotrityl Chloride Polymer)

Determination of the degree of attachment of the starting amino acids.

To 0.1 g of the polymer containing 1.43 mmol of reactive groups and pre-swollen in 5 mL dichloroethane, added was a freshly prepared solution of 0.044 g (0.1143 mmol) of Fmoc-Phe-OH and 0.040 mL (0.286 mmol) of triethylamine in 2 mL dichloroethane, and stirred with air for 25 min at 25° C. The reaction was arrested by adding 2 mL of methanol-triethylamine (9:1), and the mixture was stirred for 1 min. The peptidyl polymer was filtered off, washed with dichloroethane (2 min×3), DMF (2 min×2), isopropanol (2 min×2), DMF (2 min×2), isopropanol (2 min×2), methanol (2 min×1), and diethyl ether (2 min×2), and vacuum dried by a water jet. The extent of resin substitution was determined spectrophotometrically. To 10 mg of the thus-prepared Fmoc-Phe polymer, added was 1 mL of a 20% solution of piperidine in DMF and stirred for 20 min at 25° C. The resin was filtered off, a filtrate aliquot was taken out, and the optical absorption of the solution of the product N-(9-fluorenylmethyl)piperidine was measured at 289 nm. The extent of resin substitution was calculated from $$c = A_{289} \times V \times W / 5800,$$

where c is the active group content in the polymer, $A_{289}$ is the optical density of the solution relative to a reference, W is the weight of the polymer sample (mg), and 5800 is the molar absorptivity of N-(9-fluorenylmethyl)piperidine. The Fmoc-Phe content of the polymer was 0.3 mmol/g.

To 0.331 g of the polymer containing 0.099 mmol Cl and pre-swollen in 3.3 mL dichloroethane, added was a freshly prepared solution of 0.115 g (0.3 mmol) of Fmoc-Phe-OH and 0.034 mL (0.25 mmol) of triethylamine in 0.6 mL dichloroethane, and stirred for 25 min at 25° C. The reaction was arrested by adding 6 mL of methanol-triethylamine (9:1), and the mixture was stirred for 1 min. The peptidyl polymer was filtered off and washed with dichloroethane (2 min×3), DMF (2 min×2), isopropanol (2 min×2), DMF (2 min×2), isopropanol (2 min×2), methanol (2 min×1), and diethyl ether (2 min×2). Every portion of the wash solution was 2 mL. The synthetic cycle comprised: (1) 10-min activation of the Fmoc amino acid to be attached (3 equiv.) with DIC (3 equiv.) and HOBt (3.6 equiv.) in 1 mL DMF; (2) deblocking α-amino groups by exposure to a 20% solution of piperidine in DMF (3 mL×3) for 30 min; (3) washing the peptidyl polymer with DMF (1.5 mL×8×3 min); (4) additionally washing the peptidyl polymer with a solution of HOBt (3.6 equiv.) in 1.5 mL DMF for 3 min; (5) condensation of the activated Fmoc amino acid (3 equiv.) with the peptidyl polymer for 24 h; (6) washing the peptidyl polymer with DMF (1.5 mL×2×2 min); and (7) monitoring the completion of substitution of amino groups upon the attachment of every next Fmoc amino acid by the ninhydrin test; if the test was positive, the condensation step was repeated. Two condensation steps were carried out for the following amino acids: $Arg^2$, $Trp^3$, $Trp^4$, $Arg^5$, and $Arg^6$.

| No. | Amino acid (AA) | Reagent amounts | Condensation reaction time, h | Ninhydrin test |
|---|---|---|---|---|
| 1 | Fmoc-Arg-OH* | 0.118 g AA (0.3 mmol)<br>0.048 g HOBt (0.36 mmol)<br>0.046 mL DIC (0.3 mmol) | 24 | + |
|   | Fmoc-Arg-OH* | 0.118 g AA (0.3 mmol)<br>0.048 g HOBt (0.36 mmol)<br>0.046 mL DIC (0.3 mmol) | 2 | − |
| 2 | Fmoc-Trp-OH | 0.127 g AA (0.3 mmol)<br>0.048 g HOBt (0.36 mmol)<br>0.046 mL DIC (0.3 mmol) | 24 | + |
|   | Fmoc-Trp-OH | 0.127 g AA (0.3 mmol)<br>0.048 g HOBt (0.36 mmol)<br>0.046 mL DIC (0.3 mmol) | 3 | − |
| 3 | Fmoc-Trp-OH | 0.127 g AA (0.3 mmol)<br>0.048 g HOBt (0.36 mmol)<br>0.046 mL DIC (0.3 mmol) | 24 | + |
|   | Fmoc-Trp-OH | 0.127 g AA (0.3 mmol)<br>0.048 g HOBt (0.36 mmol)<br>0.046 mL DIC (0.3 mmol) | 3 | − |
| 4 | Fmoc-Arg-OH* | 0.118 g AA (0.3 mmol)<br>0.048 g HOBt (0.36 mmol)<br>0.046 mL DIC (0.3 mmol) | 24 | + |
|   | Fmoc-Arg-OH* | 0.118 g AA (0.3 mmol)<br>0.048 g HOBt (0.36 mmol)<br>0.046 mL DIC (0.3 mmol) | 5 | + |
|   | Fmoc-Arg-OH* | 0.118 g AA (0.3 mmol)<br>0.048 g HOBt (0.36 mmol)<br>0.046 mL DIC (0.3 mmol) | 12 | − |
| 5 | Fmoc-Arg-OH* | 0.118 g AA (0.3 mmol)<br>0.048 g HOBt (0.36 mmol)<br>0.046 mL DIC (0.3 mmol) | 16 | + |
|   | Fmoc-Arg-OH* | 0.118 g AA (0.3 mmol)<br>0.048 g HOBt (0.36 mmol)<br>0.046 mL DIC (0.3 mmol) | 16 |   |

*Prior to the reaction, the Fmoc-Arg-OH side function in DMF was converted to hydrochloride by adding one equivalent of 12N aqueous HCl. The solvents were distilled off under vacuum; drying was over NaOH.

After the synthesis was over and the α-amino group was deblocked, 0.143 g of the peptidyl polymer was washed with DMF (1 mL×8×2 min) and then with HOBt (3.6 equiv.) in 1 mL DMF.

(b) $N^\alpha$-[6(7)-(Protohemin IX)-yl]-ArgArgTrpTrpArgPhe-OH (SEQ ID NO:4, Compound XX)

To 0.29 g of the peptidyl polymer (XX) with cleaved Fmoc protection, added was 3 equiv. of protohemin IX 6(7)-mono-N-oxy-5-norbornene-2,3-dicarboximide ester (II) in 4.5 mL DMF, stirred for 5 h, and allowed to stand for 24 h at room temperature. The hemin peptidyl polymer was separated and washed with DMF (2 mL×7×3 min). The ninhydrin test was negative. The hemin peptidyl polymer was washed with DCM (2 mL×2×2 min), vacuum dried with a water-jet pump, added with 4.5 mL of TFA-TFE-DCM (1:1:8), and then stirred under a nitrogen atmosphere for 3 h. The polymer was separated and washed with TFA-TFE-DCM (1:1:8) (1 mL×4×1 min). The residue was triturated with cool anhydrous diethyl ether (taken in a 10- to 12-fold excess in volume); a precipitate was filtered off, washed twice with diethyl ether, and vacuum dried. The product was purified on a column (150×20 mm) packed with Sephadex LH-20; the target product was eluted with methanol-water (20:1). Yield: 0.027 g (25%). $R_f$:0.5 (6). Electronic spectrum (methanol), $\lambda_{max}$, nm ($\epsilon\times10^{-3}$, $M^{-1}$ $cm^{-1}$): 393.4 (65.8), 474.8 (8.7), 578.0 (3.61), 607.2 (3.19). Mass spectrum, m/z: 1605 $[M]^+$ (calc.: 1603.5).

Example 11

6,7-bis[($N^\alpha$-L-Arginyl Methyl Ester)-L-Arginyl]-Protohemin IX (Compound XXI, $R_1=R_2=$-Arg-ArgOMe)

(a) $N^\alpha,N^G,N^G$-Tribenzyloxycarbonylarginine N-Oxysuccinimide Ester

To a solution of 0.410 g (0.709 mmol) of $Z_3$ArgOH in 5 mL CLF (anhydr.) added was 0.0816 g (0.709 mmol) of N-oxysuccinimide in 1 mL DMF. The reaction mixture was cooled to –10° C., and 0.146 g (0.709 mmol) of DCC in 5 mL CLF was dropped for 10 min. The reaction mixture was stirred for 2 h at 0° C., then for 5 h at room temperature, and allowed to stand for 17 h at a temperature of 4 to 5° C. The reaction was monitored by TLC under conditions (11). A DCU precipitate was separated by twofold filtering; the solvent was removed under vacuum. The residue was crystallized by petroleum ether from ethyl acetate. The solid residue was dried under vacuum over anhydrous $CaCl_2$. Yield: 0.380 g (81%); Rf: 0.68 (11). FT-IR spectrum, $\nu$, $cm^{-1}$, KBr pellet: 1742 (CO est.), 1610 (OCONH), 1541 (OCONH), 1262 (arom.). Mass spectrum, m/z: $[M]^+$ 673.7. In [106]: mp 85-86. $[\alpha]_D^{25}$ –9.7° (C. 2; dioxane).

(b) $N^\alpha,N^G,N^G$-Tribenzyloxycarbonylarginylarginine Methyl Ester

To a suspension of 0.023 g (0.0890 mmol) of H-ArgOMe.2HCl in 2 mL DMF, added was 0.024 mL (0.178 mmol) of $Et_3N$ and stirred at room temperature for 5 min. To the resulting solution, added was 0.060 g (0.890 mmol) of the earlier prepared N-oxysuccinimide ester of $N^\alpha,N^G,N^G$-tribenzyloxycarbonylarginine mixed with 1.5 mL DMF, and was stirred for 22 h at room temperature. The reaction was monitored by TLC under conditions (2). The solvent was concentrated to 1 mL under vacuum, and 10 mL of diethyl ether was added. An oily precipitate was separated from the solvent by decantation; the residual solvent was removed under vacuum. The residue was dissolved in 15 mL of CLF:MeOH (8:2) and washed with water. The organic layer was removed under vacuum. The substance was purified by column chromatography on Kieselgel 60 $F_{254}$ silica gel (Merck, Germany) (8×3 cm); the eluent was CLF-MeOH (9:1). Fractions containing the substance with Rf of 0.48 (2) were collected. The solvent was removed under vacuum. Yield: 0.056 g (78%); Rf: 0.48 (2). FT-IR spectrum, $\nu$, $cm^{-1}$, KBr pellet: 1727 (CO est.), 1642 (amide I), 1548 (amide II). Mass spectrum, m/z: $[M]^+$ 748.

(c) 6,7-bis[($N^\alpha$-L-Arginyl Methyl Ester)-L-Arginyl]-Protohemin IX

To 0.054 g (0.0511 mmol) of $N^\alpha$-arginyl-$Z_3$-arginine methyl ester, poured was 8 mL of methanol-acetic acid-water (6:1:1). To the solution added was a palladium catalyst, and hydrogenation was carried out at room temperature for 1 h, with the reaction being monitored by TLC in system (2). When the reaction was over, the catalyst was filtered off and washed with water; the solvent was removed under vacuum at 40° C. To a suspension of the prepared H-ArgArgOMe.3$CH_3$COOH in 2 mL DMF, added was 0.0216 mL (0.1542 mmol) of $Et_3N$ and stirred at room temperature for 2 min. $Et_3N$.HCl precipitation was observed. To the resulting suspension added was a solution of 0.022 g (0.0257 mmol) of protohemin IX 6,7-bis-N-oxysuccinimide ester (I) in 1 mL DMF and stirred for 3.5 h at room temperature. The reaction was monitored by TLC under conditions (5). The solution was concentrated to 1 mL under vacuum, and 7 mL of diethyl ether was added. To introduce Cl counterions the residue was dissolved in 15 mL of CLF-MeOH (8:2), shaken two times with 7.5 mL of 0.1 N hydrochloric acid, and washed with water to a neutral reaction. The solvent was removed under vacuum. The substance was purified by preparative TLC on Kieselgel 60 $F_{254}$ silica gel (Merck, Germany) (11×14 cm); the eluent was MeOH:AcOH:$H_2O$ (4:1:1). Yield: 0.015 g (40%). Rf: 0.1 (5). Electronic spectrum, $\lambda_{max}$, nm, CLF:MeOH (8:2), ($\epsilon\times10^{-3}$): 400 (79.2), 478 (5.72), 596 (3.41). FT-IR spectrum, $\nu$, $cm^{-1}$, KBr pellet: 1739 (CO est.), 1642 (amide I), 1531 (amide II). Mass spectrum, m/z: $[M]^+$ 1270.4.

Example 12

Destructive Effect Studies of Hemin Derivatives of General Formula (I) on Lipid Membranes In studying the effect of hemin derivatives on the permeability of lipid membranes, the carboxyfluorescein (CF) release from carboxyfluorescein-loaded liposomes induced by these derivatives was measured as described in [Y. N. Antonenko, T. B. Stoilova, S. I. Kovalchuk, et al., "Large Unselective Pore in Lipid Bilayer Membrane Formed by Positively Charged Peptides Containing a Sequence of Gramicidin A," FEBS Letters, 2005, Vol. 579, pp. 5247-5252]. Liposomes were prepared using a stock solution of DOPC in chloroform with a concentration of 20 mg/mL. A 200-μL portion of the stock solution was concentrated under nitrogen flow; a 0.4-mL portion of a buffer solution containing 10 mM Tris, 10 mM MES, 100 mM KCl, and 100 mM CF was added; and the mixture was shaken for 2 min and then subjected to three freezing/thawing cycles being shaken after the end of each cycle. The resulting mixture of multilamellar liposomes was extruded through a polycarbonate filter with a pore diameter of 0.1 μm using an Avanti (Avanti Polar Lipids, USA) mini-extruder. The CF not included into liposomes was separated by gel chromatography on Sephadex G-50. The Sephadex was left overnight in water to swell. A 20-mL column was packed with swollen Sephadex and then equilibrated with 60 mL of a buffer containing 10 mM Tris, 10 mM MES, and 100 mM KCl (buffer A). The volume of the CF-containing liposome suspension was 500 μL (the lipid concentration was 0.045 mg/mL). The suspension was placed into a cell, and the volume was adjusted to 2 mL with buffer A. To the resulting liposome suspension, added was 10 μL of a $10^{-4}$ M solution of a hemin derivative of general formula (I) in DMSO. The dynamics of CF release was monitored fluorimetrically. Carboxyfluorescein fluorescence was excited at a wavelength of 490 nm and detected at 520 nm (the two slits were each 5 nm wide). A relative amount of the dye released from liposomes in a particular moment of time was calculated from $$\alpha=(F_f-F_0)/(F_m-F_0),$$

wherein $F_0$ and $F_f$ are the fluorescence level before and after the peptide is added, respectively; and $F_m$ is the fluorescence value after complete destruction of the liposomes by detergent Triton X-100, which was added to a final concentration of 2.4% (by weight).

FIG. 1 shows the dynamics of carboxyfluorescein release from liposomes under the effect of hemin derivatives of general formula (I) for the lipid/hemin derivative ratio of 10:1 (mol/mol).

Example 13

Antibacterial Activity Studies of Compounds of General Formula (I)

The antibacterial activity of compounds was determined against *Bacillus subtilis* BKM B-501, *Staphylococcus aureus* 209P, *Enterococcus faecalis* BKM B-871, and *Micrococcus luteus* BKM Ac-2230 strains (acquired from the All-Russia Collection of Microorganisms at the Institute for Biochemistry and Physiology of Microorganisms, Russian Academy of Sciences). The main parameters characterizing the antibacterial activity are the minimal inhibitory concentration (MIC) and minimal bactericidal concentration (MBC). MIC is the least concentration of a tested compound that completely inhibits the reproduction of bacteria in a liquid medium. MBC is the least concentration that causes the death of all cells.

MIC was quantified by inhibiting culture growth in a liquid medium with serial dilutions of compounds using a modified procedure [Amsterdam, D., "Susceptibility Testing of Antimicrobials in Liquid Media," in *Antibiotics in Laboratory Medicine*, Ed. by Lorian, V., 4th ed., Baltimore: Williams and Wilkins, 1996, pp. 52-111].

Bacteria were cultured and tests were carried out on an MH liquid medium (Mueller-Hinton medium: a dry extract of beef broth, 4 g/L; starch, 1.5 g/L; casein hydrolyzate, 17.5 g/L; Sigma-Fluka Catalog No. 70192) at 37° C., 100% humidity, and under stirring. Cultures (4th through 7th receeding post-thawing) in the exponential growth phase were used for tests.

All tested compound, except for gramicidin D, absorb the light at 595 nm, a wavelength used for evaluating bacterial culture growth. Therefore, a correction for absorption was applied in estimating the optical density of bacterial suspensions for each compound with account for its concentration in the well. Bacterial growth inhibition (GI) in percent after 20 hours of incubating cells with a tested compound was derived from the optical density (A) measured in every well at a wavelength of 595 nm using the equation $$GI_i = [(A_{ct} - A_{c0}) - (A_{it} - A_{i0})] \times 100/(A_{ct} - A_{c0}), \quad (1)$$

wherein the subscripts have the following meanings: i denotes the well number, c denotes a control well with bacteria whereto the tested compound is not inserted, 0 refers to the measurement taken immediately once the tested compound is inserted to the well, and t refers to the measurement taken 20 hours after the compound is inserted.

The protocol for experimental antibacterial activity determination for tested compounds was as follows. A cryovial with the test strain culture (*Bacillus subtilis* BKIVI B-501, *Staphylococcus aureus* 209P, *Enterococcus faecalis* BKM B-871, or *Micrococcus luteus* BKIVI Ac-2230) in a medium with 7% DMSO stored in liquid nitrogen, was rapidly defrosted, and 1.5 mL of the fresh MH medium was inoculated with 100 μL of the cell suspension. Cells were grown for one day at 37° C. and stirred on an orbital shaker at 150 rpm. The morphologic features of the strain and the absence of contamination with foreign bacteria were verified by: (a) inoculation on an agarized (15 g/L agar) MH medium and observation of the shape and color of the grown colonies and (b) examination of characteristic morphologic features under a microscope (Mikmed-2, LOMO, Russia) equipped with a 40× objective lens. Further bacteria were cultured in 1 mL of the liquid MH medium at 37° C. under stirring. The cells were reseeded every day. Cell cultures were used in tests starting with 3rd reseeding and ending with 6th one.

For testing, 5 μL of a bacterial suspension in the stationary growth phase was transferred to 1 mL of a sterile MH medium and incubated until the exponential growth phase was attained (3 to 5 h, 37° C., stirring at 150 rpm). To estimate the microorganisms concentration, the optical density (A) of the resulting bacterial culture was measured at a wavelength of 595 nm. The value of A=0.2 measured from a 200-4 portion of the cell suspension in a 96-well plate, with a correction for the medium absorption applied, was set to correspond to $4 \times 10^8$ cells/mL for both strains used. Taking into account the cell concentration measurements, the suspension was diluted with the MH medium to a concentration of from $5 \times 10^4$ to $1 \times 10^5$ cells/mL and transferred to a sterile 96-well plate in an amount of 100 μL, per well. Then, the cells were added with tested compounds and twofold serial dilutions of these compounds in plate's wells were made. The maximal concentration of a compound in the series was $10^{-4}$ M; the minimal one was $1.6 \times 10^{-6}$ M. The antibacterial activity studies were performed in two replicas for each compound, and the results were averaged.

The controls used were: 100 μL of an additive-free bacterial culture (four wells); a bacterial culture added with 1% DMSO or water in the same volume as in the wells with the maximal concentration of the tested compounds (four wells); and 100 μL of the sterile MH medium without bacteria and without tested compounds for control of occasional contamination in the plate (four wells).

Immediately once compounds were inserted, $A_{i0}$ was measured in every well, and $A_{c0}$ was measured in control wells using a Uniplan (Picon, Russia) plate photometer (both values were necessary for calculations by equation (1)). The plate was incubated for 20 h at 37° C. and stirred at 150 rpm. Then, $A_{it}$ was measured in every well and $A_{ct}$ in control wells, and bacterial growth inhibition was calculated from equation (1). MIC was determined as the minimal concentration of the tested compound at which growth inhibition was 100%.

In MBC determinations, the medium from wells wherein the tested compound concentration equaled MIC, MIC×2, or MIC×4 was transferred to Petri dishes with an agarized MH medium (15 g/L agar) and uniformly spread over the area of the dish using sterile spatulas. The dishes were incubated for two days. MBC was determined as the least concentration of the tested compound at which colonies were not grown on Petri dishes.

All antibacterial activity tests were repeated at a two-day interval in order to evaluate the variability of the resistance of bacterial cells toward the tested compounds.

TABLE 1

Antibacterial activity characteristics of compounds of general formula (I) against Gram-positive bacteria *Bacillus subtilis* BKM B-501

| Compound | MIC, μM | MBC, μM |
|---|---|---|
| V | 19 ± 7 | 38 ± 13 |
| VI | 38 ± 13 | 75 ± 25 |
| VII | 3.1 ± 0.8 | 3.1 ± 0.8 |
| VIII | 6.3 ± 1.6 | 9 ± 4 |
| IX | 50 ± 13 | 100 ± 25 |

TABLE 1-continued

Antibacterial activity characteristics of compounds of general formula
(I) against Gram-positive bacteria *Bacillus subtilis* BKM B-501

| Compound | MIC, μM | MBC, μM |
|---|---|---|
| XI | 12.5 ± 4 | 25 ± 7 |
| XII | 38 ± 13 | 38 ± 13 |
| XIV | 1.6 ± 0.4 | 6.3 ± 1.6 |
| XV | 12.5 ± 4 | 25 ± 7 |
| XVI | >200 | >200 |
| XVII | >200 | >200 |
| XVIII | 1.6 ± 0.4[1] | Not reached |
| XIX | 100 ± 25 | Not reached |
| Hem | 13 ± 4 | 50 ± 13 |
| Gramicidin S | 2.5 | 5 |

TABLE 2

Antibacterial activity characteristics of compounds of general formula
(I) against Gram-positive bacteria *Staphylococcus aureus* 209P

| Compound | MIC, μM | MBC, μM |
|---|---|---|
| V | 50 | >400[2] |
| VII | 50 | 200 |
| VIII | 25 | 200 |
| IX | 100 | 400 |
| XI | 12.5 | Not reached |
| XII | 50 | >50[2] |
| XIV | 1.6 | 3.2 |
| XV | 50 | 50 |
| XVI | >200 | >200 |
| XVII | >200 | >200 |
| XVIII | 6.3 | >50[2] |
| XIX | 200 | Not reached |
| Hem | 100 | 200 |
| Gramicidin S | 0.8 | 3.1 |

TABLE 3

Antibacterial activity characteristics of compounds
of general formula (I) against Gram-positive bacteria
*Enterococcus faecalis* BKM B-871

| Compound | MIC, μM | MBC, μM |
|---|---|---|
| V | 100 | 400 |
| VII | 50 | 400 |
| VIII | 12.5 | 25 |
| IX | 200 | >400[3] |
| XI | 100 | Not reached |
| XII | 50 | >50[3] |
| XIV | 25 | 100 |
| XV | 100 | Not reached |
| XVI | >200 | >200 |
| XVII | >200 | >200 |
| XVIII | 12.5 | >50[3] |
| XIX | 200 | Not reached |
| Hem | 1000 | >1000 |
| Gramicidin S | 3.1 | 6.3 |

TABLE 4

Antibacterial activity characteristics of compounds
of general formula (I) against Gram-positive bacteria
*Micrococcus luteus* BKM Ac-2230

| Compound | MIC, μM | MBC, μM |
|---|---|---|
| V | 3.1 | 6.3 |
| VI | 25 | 25 |
| VII | 1.6 | 6.3 |
| VIII | 6.3 | 12.5 |

TABLE 4-continued

Antibacterial activity characteristics of compounds
of general formula (I) against Gram-positive bacteria
*Micrococcus luteus* BKM Ac-2230

| Compound | MIC, μM | MBC, μM |
|---|---|---|
| IX | 6.3 | 25 |
| XI | 50 | 200 |
| XII | 1.6 | >6.3[3] |
| XIV | 0.8 | 1.6 |
| XV | 1.6 | 6.5 |
| XVI | >200 | >200 |
| XVII | >200 | >200 |
| XVIII | 3.1 | 12.5 |
| XIX | 25 | 25 |
| Hem | 12.5 | 25 |
| Gramicidin S | 0.4 | 0.8 |

Notes to Tables 1 to 4

[1] The compound has a bacteriostatic effect: it inhibits the reproduction of bacteria in the indicated concentration, but does not kill them.

[2,3] MBC is not reached. The value is the maximal used concentration of the compound.

Thus, compounds VII, VIII, and XVIII suppress the growth of Gram-positive bacteria *S. aureus* in concentrations of up to 50 μM (Table 2).

*M. luteus* bacteria are highly sensitive to the compounds under consideration. Compounds V, VI, VII, VIII, IX, hemin, GrD, and gramicidin S inhibit the growth of *M. luteus* in concentrations of up to 30 μM. For compounds V, VII, VIII, GrD, and gramicidin S (Table 4), MICs are rather low (lower than 10 μM). Hem and compound VI are slightly less active (MIC=12.5 and 25 μM, respectively). All tested compounds were bactericidal against *M. luteus*, and their MBCs did not exceed 30 μM.

*E. faecalis* enterococci are (on the average) more resistant to the compounds under consideration than *M. luteus* micrococci or *S. fureus* staphylococci. Compound XVIII has the highest efficacy against *E. faecalis*: MIC=12.5 μM.

All tested compounds are active against Gram-positive bacteria *B. subtilis*. Compounds VII and XVIII were most active in this regard (their MICs are less than 10 μM).

Example 14

Specific Activity Determination for Hemin Derivatives Against Resistant Bacterial Strains Materials and Methods The tested agents were water-soluble hemin derivatives (compounds VII and XVIII) or DMSO-soluble derivatives (compounds VIII, XV, and XIV). Vancomycin was the reference compound. Each compound was tested in three replicas.

Sterile single-use flat-bottomed 96-well plates, Petri dishes, pipettes, tips, and test tubes (Pan-Eco, Moscow) were used in the study.

The nutritional media used were as follows. A working Mueller Hinton broth was prepared from dry media (Mueller Hinton broth, Acumedia, Baltimore) and sterilized by autoclaving at 121° C. for 15 min.

*Staphylococcus aureus* was cultured on the Tripticase Soy Agar (BBL) commercially available dry medium. *Enterococcus faecalis* was cultured on the Columbia Agar Base (BBL) commercially available dry medium. These media were sterilized by autoclaving at 121° C. for 15 min.

Resistant Test Bacterial Strains

Gram-positive strains:

*Staphylococcus aureus* No. 25923 ATCC (American Type Culture Collection);

*Staphylococcus aureus* No. 100 KC;

*Staphylococcus epidermidis* No. 533;

*Enterococcus faecalis* No. 559;

*Enterococcus faecium* No. 569.

Bacterial inoculum was fixed and equal to $5 \times 10^5$ CFU/mL.

The results are displayed in the tables below as average values.

Experimental Strategy

For water-soluble compounds, wells from 2nd through 8th were added with the solvent (water) in an amount of 15 µL per well, then the 1st well was added with 30 µL of the stock solution of the tested compound in water with a concentration of $1 \times 10^3$ M, and the concentration was adjusted to $0.007 \times 10^3$ M by serial twofold dilutions. A 10-µL portion was taken from every well, and 190 µL of the bacterial culture ($10^5$ CFU) was added per well.

For DMSO-soluble compounds, wells from 2nd through 8th were added with the solvent (DMSO) in an amount of 10 µL per well, then the 1st well was added with 20 µL of the stock solution of the tested compound in water with a concentration of $5 \times 10^3$ M, and the concentration was adjusted to $0.039 \times 10^3$ M by serial twofold dilutions. A 2-µL portion was taken from each well, and 198 µL of the bacterial culture ($10^5$ CFU) was added per well.

The control comprised wells free of tested compounds (culture growth control). In addition, purity control of nutritional media and solvents was used. Plates were incubated in a thermostat at 36° C. for 24 hours.

Culture growth was evaluated visually by comparison of how microorganisms grew in the presence of tested compounds and in the absence of them. MSC (the minimal suppressing concentration) was set equal to the last dilution of a tested agent which suppressed bacterial culture growth.

/// The results are displayed in the tables below.

TABLE 5

MICs for hemin derivatives against Gr+ strains ($\times 10^{-5}$ M)

| Hemin derivatives | St. aureus 25923 | St. aureus 100 KC | St. epiderm 533 | Ent. faecalis 559 | Ent. faecium 569 |
|---|---|---|---|---|---|
| II | 1.0 | >1.0 | >1.0 | 0.42 | 0.33 |
| VII | 2.5 | 5.0 | 2.5 | 2.5 | >5.0 |
| VIII | 0.260 | 0.625 | 0.521 | 0.312 | >5.0. |
| XIV | 0.521 | >5.0 | 0.521 | 0.625 | >5.0 |
| XV | 2.5 | >5.0 | 2.5. | >5.0. | >5.0 |
| XVIII | 0.078 | 0.156 | 0.078 | 0.078 | 0.625 |
| XXI | 5.0 | 5.0 | 5.0 | 5.0 | >5.0 |
| Hem | >1.0 | >1.0 | >1.0 | >1.0 | >1.0 |

TABLE 6

MICs for Vancomycin against Gr+ and Gr– strains (µg/mL)

| Bacterial strain | Vancomycin |
|---|---|
| *Staphylococcus aureus* No. 25923 ATCC | 1.0 |
| *Staphylococcus aureus* No. 100 KC | 1.0 |
| *Staphylococcus epidermidis* No. 533 | 1.0 |

TABLE 6-continued

MICs for Vancomycin against Gr+ and Gr– strains (µg/mL)

| Bacterial strain | Vancomycin |
|---|---|
| *Enterococcus faecalis* No. 559 | 1.0 |
| *Enterococcus faecium* No. 569 | >32.0 |

Thus, the hemin derivatives of general formula (I) are to various degrees active against resistant Gr+ bacterial strains.

Example 15

Hemolytic Activity Determination Protocol for Compounds of General Formula (I)

Fresh human capillary blood was used in hemolytic activity studies. The hemolysis efficacy was determined as the hemoglobin release from erythrocytes in the RPMI-1640 medium (without Phenol Red and with addition of 10% fetal bovine serum and 20 mM L-glutamine) for an initial erythrocyte density of $(1.0 \pm 0.1) \times 10^7$ cells/mL after 3-h incubation with an agent (37° C., 5% $CO_2$, 100% humidity, stirring on an orbital shaker).

The hemolytic activity was characterized by the hemoglobin fraction released from erythrocytes to the external medium. Erythrocytes, erythrocyte ghosts, and intermediate species containing unreleased hemoglobin were separated by centrifugation. Hemoglobin was quantified by the absorption of the supernatant at a wavelength of 414 nm (near the Soret band maximum for the heme).

Inasmuch as all tested compounds except for GrD absorb light at this wavelength, a correction for the absorption of each compound with account for its concentration was applied in calculating the hemoglobin release fraction. The percent hemoglobin release (HR) was calculated from the optical density (A) measured at a wavelength of 414 nm using the equation $$HR = [(A_{ei} - A_{e0}) - (A_{mi} - A_{m0})] \times 100 / (A_{et} - A_{e0}), \qquad (2)$$

where the subscripts have the following meanings: e refers to the supernatant of the sample with erythrocytes, i refers to the added concentration of the tested compound, o refers to the supernatant of the sample without addition of the compound, m to the erythrocyte-free solution, and t to the supernatant of the sample where erythrocyte lysis is 100%. The hemoglobin release fraction equals the lysed erythrocyte fraction provided that lysis is complete, that is, that all the hemoglobin contained in an erythrocyte leaves it upon lysis.

Hemolytic activity studies were performed in two replicas for each compound, and the results were averaged.

The experimental protocol for hemolytic activity determination was as follows. Blood (100 µL) was collected from a finger of a healthy donor into a test tube containing 0.9 mL of the RPMI-1640 medium (without Phenol Red) and heparin (10 units/mL). Cells were sedimented by centrifugation for 5 min at 200×g and transferred to 10 mL of the RPMI-1640 medium (without Phenol Red with addition of 10% fetal calf serum and 20 mM L-glutamine; hereinafter, the complete medium). The erythrocyte density in the suspension was determined by counts in Goryachev's chamber using a Mikmed-2 (LOMO, Russia) microscope, and the suspension was diluted to $(2 \pm 0.2) \times 10^7$ cells/mL with the complete medium.

Series of solutions of tested compounds in the complete medium were prepared by serial twofold dilutions (maximal concentration: 200 µM; minimal concentration: 1.6 µM; volume: 75 μL). To the prepared solutions, 75 μL of an erythrocyte suspension with a density of $(2\pm0.2)\times10^7$ cells/mL was rapidly added.

Negative controls were prepared as follows. To 75 μL of an erythrocyte suspension with a density of $(2\pm0.2)\times10^7$ cells/mL added was: (a) 75 μL of the complete medium (four samples), (b) 60 μL of the complete medium and 15 μL of water (four samples), or (c) 73.5 μL of the complete medium and 1.5 μL of DMSO (four samples). To determine the 100% hemoglobin release (positive control; four samples), erythrocytes from a 75-μL portion of the suspension were sedimented by centrifugation (5 min at 200×g), the sediment was resuspended in deionized water (50 μL), and after lysis was complete the sample volume was adjusted to 150 μL with the complete medium.

All samples (except for the positive control) were incubated for 3 h at 37° C., 5% $CO_2$, 100% humidity, and under stirring at 150 rpm. Then, all samples were centrifuged for 5 min at 2700 g. To wells of a 96-well plate, 130 μl, of the supernatant from every sample was transferred per well. Following this, the optical density was measured in wells of the plate at a wavelength of 414 nm using a Uniplan (Picon, Russia) photometric analyzer. The hemoglobin release was calculated from relationship (2). FIG. 2 displays the hemolytic activity of hemin derivatives and reference compounds (gramicidin S, gramicidin D, and hemin) The data are presented as an average over two replicas±standard deviation.

FIG. 2.

Compound XII does not manifest hemolytic activity until its concentration is 100 μM. Compounds V, VI, VIII, IX, and XVIII have low hemolytic activities (FIG. 2); the hemolytic efficacy for all of the compounds synthesized is lower than for hemin, and is very low even for the maximal concentrations of the compounds (100 μM).

Example 16

Cytotoxic Activity Studies of Compounds of General Formula (I) against Human Leukocytes Total leukocytes were isolated from human blood by unforced sedimentation using freshly collected venous blood from a healthy donor.

Blood (10 mL) added with 10 units/mL heparin was exposed for 2.5 h in the dark at a temperature of 15 to 18° C. A light-colored liquid supernatant (4 mL) was collected over the layer of sedimenting erythrocytes, washed three times with balanced Hanks's salt solution, and resuspended in the RPMI-1640 medium (added with 8% fetal bovine serum, 2 mM L-glutamine, and 10 mM HEPES; hereinafter, the complete medium).

The concentrations of leukocytes and erythrocytes in the suspension were determined by counts in Goryachev's chamber, after which the suspension was adjusted to a leukocyte concentration of $(1.0\pm0.1)\times10^6$ cells/mL with the complete medium. The erythrocyte concentration in the blood cell suspension used for measurements did not exceed 30% of the leukocyte concentration.

To determine the cytotoxicity of the tested compounds for human leukocytes, the cell suspension was transferred to wells of sterile 96-well plates, tested compounds were added with serial twofold dilutions (the range of tested concentrations was from 3.2 to 100 μM for GrD and gramicidin S; from 8 to 500 μM for compound XIII; and from 8 to 1000 μM for compounds V, VI, VII, VIII, IX, X, XI, XIV, XV, XIX, and Hem), and the mixture was carefully stirred. The experiment was performed in two replicas.

As controls served cells added with an equivalent amount of the solvent in which tested compounds were prepared, namely: water for compounds VII and X; an aqueous solution of DMSO for compounds V, VI, VIII, and IX; and DMSO for GrD, gramicidin S, Hem, XI, XIII, XIV, XV, and XIX. An additional control was an additive-free leukocyte suspension.

Cells were incubated with tested compounds for 3 h (37° C., 5% $CO_2$, 100% humidity). Leukocyte death values were quantified using fluorescence microscopy. Staining with propidium iodide (it permeates only into dead cells nuclei) and Hoechst 33342 (it stains all nuclei) was used to recognize dead and living cells. Cells were incubated for 15 min in plates with propidium iodide and Hoechst 33342 (37° C., 5% $CO_2$), and then the plates were placed under a microscope for analysis.

The dead cell fraction was derived from the fluorescence images of cells obtained in the blue (Hoechst 33342) and red (propidium iodide) spectral ranges using an Axio Observer (Zeiss, Germany) fluorescence microscope equipped with a 10× objective lens (Plan-Neofluar 10×/0.3). The following sets of fluorescence filters were used. For propidium iodide: a 530/585-nm bandpass excitation filter, a 600-nm cut-off dichroic minor, and a 615-nm longpass barrier filter for analysis. For Hoechst 33342: a 359/372-nm bandpass excitation filter, a 395-nm cut-off dichroic mirror, and a 397-nm longpass barrier filter for analysis.

A digital camera recorded three types of cell images: (a) an image in the transmitted white light; (b) a blue fluorescence image obtained with UV excitation, and (c) a red fluorescence image obtained with green light excitation. At least four fields of view were photographed per well in various regions of a well. The results of analysis were averaged over 1000 to 1500 cells for every concentration of a tested compound.

TABLE 7

Cytotoxic activities of compounds of general formula (I) against human leukocytes

| Compound | Death of leukocytes in the presence of 1 mM of compound |
| --- | --- |
| Hem | 40 ± 2 |
| V | 5.8 ± 0.3 |
| VI | 10.5 ± 0.5 |
| VII | 8.0 ± 0.8 |
| VIII | 6.1 ± 0.3 |
| IX | 3.1 ± 0.3 |
| X | 4.9 ± 0.3 |
| XI | 8.6 ± 0.4 |
| XIII | 14 ± 2 |
| XIV | 17.5 ± 0.7 |
| XV | 13 ± 1 |
| XIX | 13 ± 1 |
| Background leukocyte death values | |
| without additives | 4.5 ± 0.7 |
| with addition of water | 4.2 ± 0.7 |
| with addition of 10% DMSO | 4.9 ± 0.4 |
| with addition of 100% DMSO | 8.1 ± 0.7 |

Compounds V, VII, VIII, IX, and X in concentrations of up to 1 mM did not cause the death of human blood leukocytes. A small toxic effect of solutions of gramicidin S and compound XI in DMSO was fully due to the toxic effect of the solvent (DMSO). For compounds VI, XIII, XIV, XV, and XIX, a weak toxic effect was discovered to appear at concentrations of near 1 mM for compounds XIV, XV, and XIX and at concentrations greater than 125 µM for compounds VI and XIII. The reference compound (hemin) was considerably more toxic for leukocytes compared to the claimed compounds (40% against 3-17%; Table 7).

/// The results prove the promise of the claimed compounds for creating on their base nontoxic biocompatible antimicrobial agents, in particular for the prophylaxis and treatment of diseases caused by various Gram-positive bacteria, in particular resistant ones.

Example 17

Antifungal Activity Studies of Compounds of General Formula (I)

The subjects of action were *Cryptococcus neoformans* No. 3465 museum strain cells and *Candida albicans* No. 927 museum strain cells grown for one day on a glucose-peptone-yeast medium at 32° C. The reference compounds were the following antimycotics: pimafucin, amphotericin, and fluconazole.

Experiments were carried out on round-bottomed 96-well plates (Lenmedpolimer) in two replicas. To the first column (0), added was 10 µL of the stock solution of a water-soluble agent with concentrations of $10^{-2}$ to $10^{-3}$ mol/L; to the second column, added was also the same 10 µL plus 10 µL of the solvent corresponding to the given compound, suspended, 10 µL was transferred to the next well, and so on to the 8th well of the row. Stock solutions of water-insoluble compounds of general formula (I) (compounds V, VIII, XII, XIII, XIV, and hemin) were prepared in DMSO and were diluted with DMSO and the medium. DMSO concentrations in the reaction mixture in a well were ≤5%.

Then, to every well added was 190 µL of a *Cr. neoformans* cell culture suspension in a synthetic nutritional medium (so that the final cell concentration was approximately 103 CFU/mL), this medium containing Bromocresol Blue as a pH-indicator (pH: 5.5; indicator color: blue). As pH reduced to 4.5, the indicator in the culture changed its color to yellow, thereby indicating fungal cell growth. The synthetic medium comprised the following components: salts, amino acids, microelements, vitamins, an antibiotic, and glucose (30 components altogether) [Yarrow, D., "Methods for the Isolation, Maintenance and Identification of Yeasts," in: *The Yeasts. A Taxonomic Study*, Ed. by Kurtsman, C. P, and Fell, M., Elsevier, 1998, pp. 77-100]. After being inoculated with a *Cr. neoformans* cell suspension, the plate was incubated at 32° C. for 1 h with stirring, then transferred to a stationary thermostat and incubated for two and five days at 27° C. After being inoculated with a *C. albicans* cell suspension, the plates were incubated for 1 h at 32° C. with stirring, then transferred to a stationary thermostat and incubated for one and four days at 27° C.

The results are displayed in Tables 8 and 9 below.

TABLE 8

*Cryptococcus neoformans* culture growth in the presence of compounds of general formula (I)

| | Agent | Test culture growth at various dilutions of the agent on day 2 | | | | | | | |
|---|---|---|---|---|---|---|---|---|---|
| | | 0<br>$5.00 \times 10^{-5}$ M | :2 | :4 | :8 | :16 | :32 | :64 | :128 |
| 1 | Gramicidin S | − | − | − | − | − | + | + | + |
| 2 | Hem | ± | ± | ± | ± | ± | ± | + | + |
| 3 | V | ± | ± | ± | ± | ± | ± | ± | + |
| 4 | VII | − | ± | + | + | + | + | + | + |
| 5 | VIII | ± | ± | ± | + | + | + | + | + |
| 6 | XVIII | − | − | − | − | + | + | + | + |
| 7 | Control | + | + | + | + | + | + | + | + |
| 8 | Amphotericin B | −** | − | − | − | − | − | − | − |
| 9 | Fluconazole | ±** | ± | ± | + | + | + | + | + |

(−) No growth; the indicator is blue;
(±) Weak growth; the indicator is yellow, but the precipitate of grown cells looks as a diffuse spot;
(+) Strong growth; the indicator is yellow, and the cell precipitate looks as a compact spot;
*On day 2, blue color is observed up to the 6th well but with a small precipitate on the bottom; yellow color appears on day 5;
**The agent concentration in the 0th well is $5.00 \times 10^{-4}$ M.

TABLE 9

*Candida albicans* culture growth in the presence of compounds of general formula (I)

| | Test culture growth at various dilutions of the agent | | | | | | |
|---|---|---|---|---|---|---|---|
| Agent | 0<br>$1 \times 10^{-4}$ M | :2 | :4 | :8 | :16 | :32 | :64 |
| Gramicidin S | − | − | − | − | + | + | + |
| Hem | ± | + | + | + | + | + | + |
| V | − | − | ± | ± | ± | ± | ± |
| VII | ± | + | + | + | + | + | + |
| VIII | ± | ± | ± | + | + | + | + |
| XII | ± | ± | ± | + | + | + | + |
| XIII | ± | ± | + | + | + | + | + |
| XIV | ± | + | + | + | + | + | + |
| XV | ± | + | + | + | + | + | + |
| XVIII | − | − | − | ± | ± | ± | ± |
| XX | ± | ± | ± | ± | ± | ± | ± |
| Control | + | + | + | + | + | + | + |
| Pimafucin | − | − | − | − | − | + | + |

Control inoculations from wells carried out on day 1 to 4 post-exposure to compounds of general formula (I), showed a practically fungicidal effect of compound XVIII in concentrations of about $5\times10^{-5}$ M.

Further, compound XII appeared efficacious against one cryptococcosis causative agent (*Cryptococcus humicolus*) with an MSC of 12.5 µM.

Thus, compounds of general formula (I) exert a fungistatic and/or fungicidal effects, where the size of the effect is structure dependent and manifests itself in the range of concentrations from $10^{-4}$ to $10^{-6}$ M.

Example 18

Example Dosage Forms

A. Gelatin Capsules

The powder to be introduced into capsules is formulated as follows:

| | |
|---|---|
| A compound corresponding to the general formula (I) | 1 to 50 mg |
| Magnesium oxide | 50 mg |
| Starch | 100 to 200 mg |

The above-listed ingredients are blended, and the blend is introduced into hard gelatin capsules in an amount of from 151 to 285 mg.

B. Tablet Dosage Form

A tablet dosage form is manufactured using the ingredients listed below:

| | |
|---|---|
| A compound corresponding to the general formula (I) | 1 to 50 mg |
| Potato starch | 100 mg |
| Polyvinylpyrrolidone | 10 mg |
| Magnesium stearate | 2 mg |
| Lactose | 48 to 82 mg |
| Aerosil | 5 mg |

The components are blended and compacted to produce tables each weighing 200 mg.

C. Aerosol Dosage Form

An aerosol blend intended for 10-time administration is formulated as follows:

| | |
|---|---|
| A compound corresponding to the general formula (I) | 10 to 100 mg |
| Magnesium sulfate | 150 mg |
| Lactose | 110 to 140 mg |

The compound is blended with excipients, and the blend is transferred into a special spraying device.

D. Suppositories

The following suppository bases can be used:

water-insoluble bases (cocoa butter);

water-soluble or water-miscible bases (gelatin-glycerol or polyethylene oxide); and combination (soap-glycerol) bases.

An example suppository formulation:

A compound corresponding to the general formula (I) in an amount of 1 to 50 mg, and Cocoa butter in an amount necessary for a suppository to be obtained.

When necessary, rectal, vaginal, or urethral suppositories with appropriate excipients can be manufactured.

E. Ointments

The following ointment bases can be used:

hydrocarbon ointment bases, such as white Vaseline and yellow Vaseline (Vaselinum album and Vaselinum flavum, respectively), Vaseline oil (Oleum Vaselini), and white ointment and liquid ointment (Unguentum album and Unguentum flavum, respectively), with thickening additives such as solid paraffin and wax;

absorptive ointment bases, such as hydrophilic Vaseline (Vaselinum hydrophylicum), lanoline (Lanolinum), and cold cream (Unguentum leniens);

water-removable ointment bases, such as hydrophilic ointment (Unguentum hydrophylum); water-soluble ointment bases, such as polyethylene glycol ointment (Unguentum Glycolis Polyaethyleni); bentonite bases; and others.

An example ointment formulation:

| | |
|---|---|
| A compound corresponding to general formula (I) | 0.01 g to 0.1 g |
| Vaseline | 10 g |

Ointments are prepared by the proper technologies.

E. Solution for Injections

The solvents useful to prepare solutions for injection include 0.9% sodium chloride solution, distilled water, and Novocain solution. Unit dosage forms may be manufactured as ampoules, vials, and ampins.

The formulation of the solution for injection is as follows:

| | |
|---|---|
| A compound corresponding to the general formula (I) | 1-50 mg |
| Distilled water | 1 to 2 mL |

Injection dosage forms may be manufactured as sterile solutions, sterile powders, and sterile tablets.

Example Formulations for Disinfectant and Antiseptic Agents

| | |
|---|---|
| A. A compound corresponding to the general formula (I) | 0.001 to 1% |
| 1-Propanol | 30 to 40% |
| 2-Propanol | 10 to 70% |
| Distilled water | 10 to 60% |
| B. A compound corresponding to the general formula (I) | 0.001 to 1% |
| A quaternary ammonium base (or a mixture thereof) | 2 to 10% |
| Distilled water | Up to 100% |
| C. A compound corresponding to the general formula (I) | 0.001 to 1% |
| Dimethyl sulfoxide (DMSO) | 1 to 20% |
| or polyethylene glycol (PEG) with MM = 200 to 12 000 | 1 to 20% |
| Distilled water | Up to 100% |
| D. A compound corresponding to the general formula (I) | 0.001 to 1% |
| A mixture of alcohols, DMSO, PEG, and surfactants in various combinations and proportions | 1 to 80% |
| Distilled water | Up to 100% |
| E. Compounds corresponding to the general formula (I) | 0.001 to 1% |
| Distilled water | Up to 100% |

Thus, hemin derivatives of general formula (I) have antibacterial and antifungal activities, in particular against human-pathogenic *S. aureus* and its resistant strains. Further, almost all of the claimed hemin derivatives are capable (in various degrees) of increasing the permeability of model lipid membranes, which is known from the literature to be an important part of the mechanism of the antimicrobial (antibacterial, antifungal) effect of antimicrobial agents. The efficacy of the compounds of general formula (I) proves their suitability for large-scale use in formulations of disinfectant, antiseptic, and therapeutic agents having an antifungal and antibacterial effect.

The invention claimed is:

1. A compound of general formula (I)

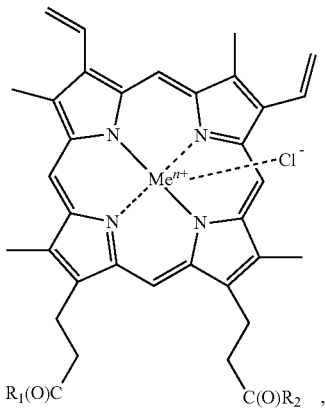

wherein either one of $R_1$ and $R_2$ is —OH and the other is -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), —N$^\delta$-cyclo-(Orn-Leu-D-Phe-Pro-Val)$_2$ (gramicidin S), -Arg-Gly-Asp-OH or -Arg-Arg-Trp-Trp-Arg-Phe-OH (SEQ ID NO:4);
or $R_1$ and $R_2$ are each —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe, wherein HA is the histamine moiety

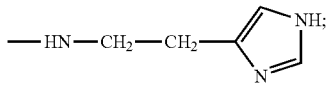

and Me$^{n+}$ is Fe$^{2+}$ or Fe$^{3+}$,
or an isomer or a mixture of isomers thereof, or a pharmaceutically acceptable salt thereof.

2. The compound according to claim 1, wherein one of $R_1$ and $R_2$ is —OH and the other is -Arg-Gly-Asp-OH, or an isomer or a mixture of isomers thereof, or a pharmaceutically acceptable salt thereof.

3. The compound according to claim 1, wherein one of $R_1$ and $R_2$ is —OH and the other is
-Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH,
wherein X=Trp, Phe or Tyr, (SEQ ID NO:3, gramicidin D), or an isomer or a mixture of isomers thereof, or a pharmaceutically acceptable salt thereof.

4. An antiseptic and/or disinfectant composition, comprising the hemin derivative of general formula (I) of claim 1.

5. A pharmaceutical composition having an antimicrobial activity, which comprises as an active ingredient the hemin derivative of formula (I) of claim 1 formulated with a pharmaceutically acceptable carrier or excipient.

6. A method of treating a microbial infection in a patient, the method comprising administering to a patient in need thereof the compound of claim 1.

7. The method of claim 6, wherein either one of $R_1$ and $R_2$ is —OH and the other is -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), —N$^\delta$-cyclo-(Orn-Leu-D-Phe-Pro-Val)$_2$ (gramicidin S), -Arg-Gly-Asp-OH or -Arg-Arg-Trp-Trp-Arg-Phe-OH (SEQ ID NO:4); or $R_1$ and $R_2$ are each —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe, wherein HA is the histamine moiety

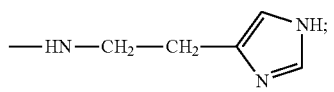

8. The method of claim 6, wherein one of $R_1$ and $R_2$ is —OH and the other is -Arg-Gly-Asp-OH, or an isomer or a mixture of isomers thereof, or a pharmaceutically acceptable salt thereof.

9. The method of claim 6, wherein one of $R_1$ and $R_2$ is —OH and the other is
-Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH,
wherein X=Trp, Phe or Tyr, (SEQ ID NO:3, gramicidin D), or an isomer or a mixture of isomers thereof, or a pharmaceutically acceptable salt thereof.

10. An antimicrobial composition, comprising an agent which is a hemin derivative of general formula (I)

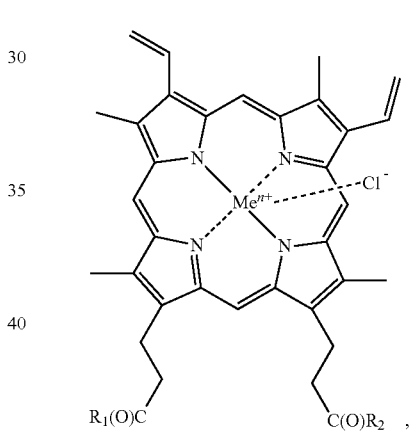

wherein
either one of $R_1$ and $R_2$ is —OH and the other is
-Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), —N$^\delta$-cyclo-(Orn-Leu-D-Phe-Pro-Val)$_2$ (gramicidin S), -Arg-Gly-Asp-OH, or -Arg-Arg-Trp-Trp-Arg-Phe-OH (SEQ ID NO:4);
or $R_1$ and $R_2$ are each —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe,
wherein HA is the histamine moiety

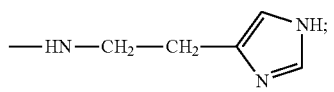

and Me$^{n+}$ is Fe$^{2+}$ or Fe$^{3+}$;
or an isomer or mixture of isomers thereof, or a pharmaceutically acceptable salt thereof.

11. A method of treating a microbial infection in a patient, wherein the microbial infection is a bacterial infection or a fungal infection, the method comprising administering to a patient in need thereof a compound of general formula (I)

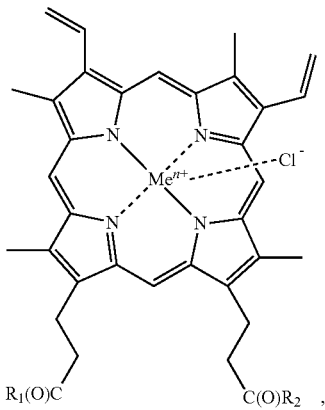

wherein
either one of $R_1$ and $R_2$ is —OH and the other is -ArgArgTrpHisArgLeuLysGlu(OMe)OH (SEQ ID NO:1), -ArgTrpHisArgLeuLysGlu(OMe)OH (SEQ ID NO:2), or -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), —N$^\delta$-cyclo-(Orn-Leu-D-Phe-Pro-Val)$_2$ (gramicidin S), -Arg-Gly-Asp-OH, or -Arg-Arg-Trp-Trp-Arg-Phe-OH (SEQ ID NO:4;
or $R_1$ and $R_2$ are each -ArgOMe, -SerOMe, -βAlaHA, βAlaHis, —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe,
wherein HA is the histamine moiety

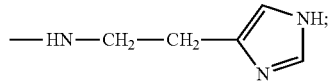

and Me$^{n+}$ is Fe$^{2+}$ or Fe$^{3+}$;
or isomers or mixtures of isomers thereof, or a pharmaceutically acceptable salt thereof.

12. The method according to claim 11, wherein the microbial infection is a bacterial infection.

13. The method according to claim 12, wherein said bacterial infection is caused by a bacterial genus selected from the group consisting of Gram-positive *Staphylococcus, Bacillus, Enterococcus*, and/or *Micrococcus*.

14. The method according to claim 13, wherein the bacterial infection is caused by a bacterial species selected from the group consisting of *Staphylococcus aureus, Enterococcus faecalis*, and *Micrococcus luteus*.

15. The method according to claim 13, wherein the bacterial infection is caused by a bacterial strain selected from the group consisting of *Staphylococcus aureus* 209P, *Enterococcus faecalis* BKM B-871, *Micrococcus luteus* BKM Ac-2230, *Staphylococcus aureus* No. 25923 ATCC, *Staphylococcus aureus* No. 100 KC, *Staphylococcus epidermidis* No. 533, *Enterococcus faecalis* No. 559, and *Enterococcus faecium* No. 569.

16. The method according to claim 11, wherein the microbial infection is a fungal infection.

17. The method according to claim 16, wherein said fungal infection is caused by a microfungal genus selected from the group consisting of *Candida* and/or *Cryptococcus*.

18. The method according to claim 17, wherein the fungal infection is caused by a microfungal species that is *Cryptococcus neoformans* or *Candida albicans*.

19. The method according to claim 16, wherein the fungal infection is caused by a microfungal strain that is *Candida albicans* No. 927 or *Cryptococcus neoformans* No. 3465.

20. The method according to claim 11, wherein in compounds of general formula (I)
either one of $R_1$ and $R_2$ is —OH and the other is -Val-Gly-Ala-(D-Leu)-Ala-(D-Val)-Val-(D-Val)-Trp-(D-Leu)-X-(D-Leu)-Trp-(D-Leu)-Trp-NHCH$_2$CH$_2$OH, wherein X=Trp, or Phe, or Tyr (SEQ ID NO:3, gramicidin D), —N$^\delta$-cyclo-(Orn-Leu-D-Phe-Pro-Val)$_2$ (gramicidin S), -Arg-Gly-Asp-OH or -Arg-Arg-Trp-Trp-Arg-Phe-OH (SEQ ID NO:4);
or $R_1$ and $R_2$ are each —NHCH$_2$CH$_2$OH, -GlyOMe, —NHCH(CH$_2$OH)CH$_2$OH, —NHCH$_2$CH(OH)CH$_2$OH, -Glu(ArgOMe)-ArgOMe, -HA, or -Arg-ArgOMe,
wherein HA is the histamine moiety

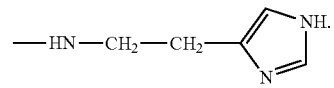

21. A process for producing a compound of formula (I) of claim 1, the process comprising reacting a hemin derivative activated at carboxy group(s) with an amino component.

* * * * *